US012173341B2

(12) United States Patent
Bae et al.

(10) Patent No.: US 12,173,341 B2
(45) Date of Patent: Dec. 24, 2024

(54) METHOD FOR PRODUCING L-AMINO ACIDS USING MICROORGANISM CONTAINING NADP-DEPENDENT GLYCERALDEHYDE-3-PHOSPHATE DEHYDROGENASE

(71) Applicant: CJ CHEILJEDANG CORPORATION, Seoul (KR)

(72) Inventors: Jee Yeon Bae, Seoul (KR); Byoung Hoon Yoon, Seoul (KR); Su Yon Kwon, Seoul (KR); Kyungrim Kim, Seoul (KR); Ju Eun Kim, Seoul (KR); Hyo Jeong Byun, Seoul (KR); Seung Hyun Cho, Seoul (KR); Nara Kwon, Seoul (KR); Hyung Joon Kim, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 588 days.

(21) Appl. No.: 17/423,262

(22) PCT Filed: Jan. 21, 2021

(86) PCT No.: PCT/KR2021/000823
§ 371 (c)(1),
(2) Date: Jul. 15, 2021

(87) PCT Pub. No.: WO2021/150029
PCT Pub. Date: Jul. 29, 2021

(65) Prior Publication Data
US 2022/0348973 A1 Nov. 3, 2022

(30) Foreign Application Priority Data
Jan. 21, 2020 (KR) .................. 10-2020-0008025

(51) Int. Cl.
*C12P 13/04* (2006.01)
*C12N 1/20* (2006.01)
*C12N 9/02* (2006.01)
*C12N 15/77* (2006.01)
*C12R 1/15* (2006.01)

(52) U.S. Cl.
CPC ............. *C12P 13/04* (2013.01); *C12N 1/205* (2021.05); *C12N 9/0008* (2013.01); *C12N 15/77* (2013.01); *C12Y 102/01012* (2013.01); *C12N 2800/101* (2013.01); *C12R 2001/15* (2021.05)

(58) Field of Classification Search
CPC ....... C12P 13/04; C12N 1/205; C12N 9/0008; C12N 15/77; C12N 2800/101; C12N 1/20; C12Y 102/01012; C12Y 102/01009; C12R 2001/15; C07K 14/34
See application file for complete search history.

(56) References Cited

U.S. PATENT DOCUMENTS

| | | | |
|---|---|---|---|
| 9,365,875 B2 * | 6/2016 | Bindel | ............. C12N 1/16 |
| 2006/0257983 A1 | 11/2006 | Bro et al. | |
| 2010/0009418 A1 | 1/2010 | San et al. | |
| 2012/0208245 A1 | 8/2012 | Rah et al. | |
| 2014/0154760 A1 | 6/2014 | Bindel | |

FOREIGN PATENT DOCUMENTS

| | | |
|---|---|---|
| KR | 10-0057684 B1 | 12/1992 |
| KR | 10-0073610 B1 | 5/1994 |
| KR | 10-0159812 B1 | 8/1998 |
| KR | 10-0292299 B1 | 3/2001 |
| KR | 10-2006-0078687 A | 7/2006 |
| KR | 10-0620092 B1 | 9/2006 |
| KR | 10-0791659 B1 | 12/2007 |
| KR | 10-0924065 B1 | 10/2009 |
| KR | 10-1117022 B1 | 2/2012 |
| KR | 10-1182033 B1 | 9/2012 |
| KR | 10-1335789 B1 | 11/2013 |
| KR | 10-1632642 B1 | 6/2016 |
| KR | 10-2017-0002574 A | 1/2017 |
| KR | 10-1783170 B1 | 9/2017 |
| KR | 10-1796830 B1 | 11/2017 |
| KR | 10-1851898 B1 | 4/2018 |

(Continued)

OTHER PUBLICATIONS

Xu, Jianzhong, et al. "Metabolic engineering Corynebacterium glutamicum for the L-lysine production by increasing the flux into L-lysine biosynthetic pathway." Amino Acids 46 (2014): 2165-2175. (Year: 2014).*

Zhang, Meiling, David A. Case, and Jeffrey W. Peng. "Propagated perturbations from a peripheral mutation show interactions supporting WW domain thermostability." Structure 26.11 (2018): 1474-1485. (Year: 2018).*

K Singh, Raushan, et al. "Protein engineering approaches in the post-genomic era." Current Protein and Peptide Science 19.1 (2018): 5-15. (Year: 2018).*

Wang et al. (2018, Published online: Jul. 18, 2018, Archives of Microbiology, doi.org/10.1007/s00203-018-1552-9, { herein Wang} (Year: 2018).*

(Continued)

*Primary Examiner* — Paul J Holland
*Assistant Examiner* — Erica Nicole Jones-Foster
(74) *Attorney, Agent, or Firm* — Morgan, Lewis & Bockius LLP

(57) ABSTRACT

The present disclosure relates to a microorganism of the genus *Corynebacterium* having an increased L-amino acid producing ability, containing NADP-dependent glyceraldehyde-3-phosphate dehydrogenase derived from the genus *Lactobacillus*. According to the present disclosure, the NADP-dependent glyceraldehyde-3-phosphate dehydrogenase derived from *Lactobacillus delbrueckii* subsp. *bulgaricus* is introduced to increase the reducing power through the activity of NADP-dependent glyceraldehyde-3-phosphate dehydrogenase, thereby increasing the L-amino acid producing ability of the strains belonging to the genus *Corynebacterium*.

20 Claims, No Drawings

Specification includes a Sequence Listing.

(56) References Cited

FOREIGN PATENT DOCUMENTS

| KR | 10-2018-0077008 A | 7/2018 |
|---|---|---|
| KR | 10-2019-0009872 A | 1/2019 |
| KR | 10-1947959 B1 | 2/2019 |
| KR | 10-2011994 B1 | 8/2019 |
| WO | 2013/081296 A1 | 6/2013 |
| WO | 2019/017706 A2 | 1/2019 |

OTHER PUBLICATIONS

Dong et al., "CRISPR-Cpf1-Assisted Engineering of Corynebacterium glutamicum SNK118 for Enhanced L-Ornithine Production by NADP-Dependent Glyceraldehyde-3-Phosphate Dehydrogenase and NADH-Dependent Glutamate Dehydrogenase," Applied Biochemistry and Biotechnology (191): 955-967 (2020).

Extended European Search Report issued in corresponding European Patent Application No. 21724998.6 dated Feb. 9, 2022.

GenBank Accession # WP_011543932, NADP-dependent glyceraldehyde-3-phosphate dehydrogenase [Lactobacillus delbrueckii].

Takeno et al., "Engineering of Corynebacterium glutamicum with an NADPH-Generating Glycolytic Pathway for L-Lysine Production," Applied and Environmental Microbiology, 76 (21): 7154-7160 (2010).

Xu et al., "Metabolic engineering Corynebacterium glutamicum for the L-lysine production by increasing the flux into L-lysine biosynthetic pathway," Amino Acids (2014).

Spaans et al., "NADPH-generating systems in bacteria and archaea," Frontiers in Microbiology, 6:742 (2015).

GenBank Accession #. WP_010966919.1, Multispecies: NADP-dependent glyceraldehyde-3-phosphate dehydrogenase [Clostridium].

GenBank Accession #. NC_015687.1, Clostridium acetobytylicum DSM 1731, complete sequence.

Binder et al., "A high-throughput approach to identify genomic variants of bacterial metabolite producers at the single-cell level," Genome Biology, 13:R40 (2012).

Guo et al., "Generation of Branched-chain Amino Acids Resistant Corynebacterium glutamicum Acetohydroxy Acid Synthase by Site-directed Mutagenesis," Biotechnology and Bioprocess Engineering, 19(3): 456-467 (2014).

Morbach et al., "L-Isoleucine Production with Corynebacterium glutamicum: Further Flux Increase and Limitation of Export,"Applied and Environmental Microbiology, 62(12): 4345-4351 (1996).

* cited by examiner

METHOD FOR PRODUCING L-AMINO ACIDS USING MICROORGANISM CONTAINING NADP-DEPENDENT GLYCERALDEHYDE-3-PHOSPHATE DEHYDROGENASE

SEQUENCE LISTING SUBMISSION VIA EFS-WEB

A computer readable text file, entitled "SequenceListing.txt," created on Aug. 11, 2021 with a file size of 22,949 bytes contains the sequence listing for this application and is hereby incorporated by reference in its entirety.

TECHNICAL FIELD

The present disclosure relates to a microorganism of the genus *Corynebacterium* having an increased L-amino acid producing ability, containing NADP-dependent glyceraldehyde-3-phosphate dehydrogenase, and a method for producing L-amino acids using the same.

BACKGROUND ART

The microorganisms of the genus *Corynebacterium* are Gram-positive microorganisms that are frequently used in industrial production of substances with various applications, such as feeds, pharmaceuticals, and foods including L-amino acids and various nucleic acids. In recent years, diamines and keto-acids have been produced from the microorganisms of the genus *Corynebacterium*.

In order to produce useful products through microbial fermentation, the demand for an energy source or reducing power has increased, along with that for strengthening the biosynthetic pathway of a target product in microorganisms. Among these, NADPH (nicotinamide adenine dinucleotide phosphate) is an essential element in providing reducing power. The oxidized form $NADP^+$ and the reduced form NADPH are in vivo electron transfer materials and are involved in various synthesis processes. Among the central metabolic pathways, NADPH is known to be mainly produced by 1) the oxidative pentose phosphate pathway and 2) the NADP-dependent isocitrate dehydrogenase (lcd gene) of the TCA pathway. In addition, various microorganisms have malate enzyme, glucose dehydrogenase, and non-phosphorylating glyceraldehyde-3-phosphate dehydrogenase as various alternative pathways to supply NADPH.

Further, regardless of the central metabolic pathway, NADPH-producing enzymes include transhydrogenase, Ferredoxin:$NADP^+$ oxidoreductase, etc. (Spaans et al., 2015, NADPH-generating systems in bacteria and archaea, *Front. Microbiol.* 6:742).

DISCLOSURE

Technical Problem

The present inventors have made intensive efforts to increase production of each amino acid in amino acid-producing microorganisms, and as a result, through various studies for introducing NADP-dependent glyceraldehyde-3-phosphate dehydrogenase, they have confirmed that the production of amino acids and precursors thereof is increased in microorganisms of the genus *Corynebacterium*, thereby completing the present disclosure.

Technical Solution

An object of the present disclosure is to provide a method for producing L-amino acids, comprising: culturing a microorganism of the genus *Corynebacterium* containing NADP-dependent glyceraldehyde-3-phosphate dehydrogenase, which includes an amino acid sequence of SEQ ID NO: 1, in a medium; and recovering L-amino acids from the cultured microorganism or cultured medium.

Another object of the present disclosure is to provide a microorganism of the genus *Corynebacterium* having an increased L-amino acid producing ability, containing NADP-dependent glyceraldehyde-3-phosphate dehydrogenase, which includes an amino acid sequence of SEQ ID NO: 1.

Still another object of the present disclosure is to provide the use of L-amino acid production of a microorganism of the genus *Corynebacterium* containing NADP-dependent glyceraldehyde-3-phosphate dehydrogenase, which includes an amino acid sequence of SEQ ID NO: 1.

Advantageous Effects

According to the present disclosure, a gene encoding gapN derived from *Lactobacillus delbrueckii* subsp. *bulgaricus* is introduced to increase the reducing power through the activity of gapN, thereby increasing the L-amino acid producing ability of the microorganism of the genus *Corynebacterium*.

DETAILED DESCRIPTION OF THE INVENTION

The present disclosure will be described in detail as follows. Meanwhile, each description and embodiment disclosed herein may also be applied to other descriptions and embodiments. That is, all combinations of various elements disclosed herein fall within the scope of the present disclosure. Further, the scope of the present disclosure is not limited by the specific description below.

To achieve the above objects, one aspect of the present disclosure is to provide a method for producing L-amino acids, comprising: culturing a microorganism of the genus *Corynebacterium* containing NADP-dependent glyceraldehyde-3-phosphate dehydrogenase, which includes an amino acid sequence of SEQ ID NO: 1, in a medium, and recovering L-amino acids from the cultured microorganism or cultured medium.

In the present disclosure, the term "NADP-dependent glyceraldehyde-3-phosphate dehydrogenase" refers to a polypeptide having an activity of converting glyceraldehyde-3-phosphate as a substrate into 3-phosphoglycerate using NADP as a coenzyme. Examples of the NADP-dependent glyceraldehyde-3-phosphate dehydrogenase may include NADP-dependent glyceraldehyde-3-phosphate dehydrogenase that is derived from animals, plants, and bacteria. Specifically, the NADP-dependent glyceraldehyde-3-phosphate dehydrogenase may be derived from bacteria, more specifically, derived from *Lactobacillus* sp., and from *Lactobacillus delbrueckii* subsp. *bulgaricus*. The NADP-dependent glyceraldehyde-3-phosphate dehydrogenase may be, for example, a polypeptide including an amino acid sequence of SEQ ID NO: 1. The polypeptide including the amino acid sequence of SEQ ID NO: 1 may be used interchangeably with a polypeptide having the amino acid sequence of SEQ ID NO: 1 or a polypeptide consisting of the amino acid sequence of SEQ ID NO: 1.

In the present disclosure, SEQ ID NO: 1 refers to an amino acid sequence having the activity of NADP-dependent glyceraldehyde-3-phosphate dehydrogenase. Specifically, SEQ ID NO: 1 may be a polypeptide sequence having the activity of NADP-dependent glyceraldehyde-3-phosphate dehydrogenase encoded by the gapN gene. For the purpose of the present disclosure, the polypeptide may be derived from *Lactobacillus* sp. and specifically from *Lactobacillus delbrueckii* subsp. *bulgaricus*, but is not limited thereto, and may include any sequence without limitation as long as it has the same activity as the amino acid. The amino acid sequence of SEQ ID NO: 1 may be obtained from NIH GenBank, a known database. Additionally, although the polypeptide having the NADP-dependent glyceraldehyde-3-phosphate dehydrogenase activity is defined in the present disclosure as the polypeptide having the amino acid sequence of SEQ ID NO: 1, it does not exclude a mutation that may occur by a meaningless sequence addition upstream or downstream of the amino acid sequence of SEQ ID NO: 1 or that may occur naturally, or a silent mutation thereof. It is apparent to those skilled in the art that any polypeptide having the same or corresponding activity to the polypeptide including the amino acid sequence of SEQ ID NO: 1 may fall within the scope of the polypeptide having the activity of NADP-dependent glyceraldehyde-3-phosphate dehydrogenase of the present disclosure. In a specific example, the polypeptide having the activity of NADP-dependent glyceraldehyde-3-phosphate dehydrogenase of the present disclosure may be a polypeptide having the amino acid sequence of SEQ ID NO: 1 or a polypeptide composed of an amino acid sequence having a homology or identity of 80%, 85%, 90%, 95%, 96%, 97%, 98%, or 99% or more to the amino acid sequence of SEQ ID NO: 1. Further, it is apparent that any polypeptide having an amino acid sequence, in which part of the amino acid sequence is deleted, modified, substituted, or added, may also fall within the scope of the polypeptide targeted for modification of the present disclosure as long as it includes an amino acid sequence having such a homology or identity and exhibiting an effect corresponding to that of the above polypeptide.

That is, in the present disclosure, although it is described as "a protein or polypeptide composed of an amino acid sequence of a particular SEQ ID NO", it is apparent that any polypeptide which has deletion, modification, substitution, or addition in part of the amino acid sequence may also be used in the present disclosure, as long as the polypeptide has the same or corresponding activity to the polypeptide composed of the amino acid sequence of the corresponding SEQ ID NO. For example, it is apparent that the "polypeptide composed of the amino acid sequence of SEQ ID NO: 1" may fall within the scope of the "polypeptide composed of the amino acid sequence of SEQ ID NO: 1" as long as the polypeptide has the same or corresponding activity.

In the present disclosure, the gene encoding the NADP-dependent glyceraldehyde-3-phosphate dehydrogenase is the gapN gene, and the gene may be derived from bacteria, and more specifically, derived from a microorganism of the genus *Lactobacillus*, but the microorganism is not particularly limited as long as it is a microorganism of the genus *Lactobacillus* capable of expressing the gapN gene. Specifically, the microorganism of the genus *Lactobacillus* may be *Lactobacillus delbrueckii* subsp. *bulgaricus*. The gene may be a nucleotide sequence encoding the amino acid sequence of SEQ ID NO: 1, and more specifically, a sequence including a nucleotide sequence of SEQ ID NO: 2, but is not limited thereto. The polynucleotide including the nucleotide sequence of SEQ ID NO: 2 may be used interchangeably with a polynucleotide having the nucleotide sequence of SEQ ID NO: 2 and a polynucleotide composed of the nucleotide sequence of SEQ ID NO: 2.

As used herein, the term "polynucleotide", which refers to a polymer of nucleotides composed of nucleotide monomers connected in a lengthy chain by covalent bonds, means a DNA or RNA strand having at least a certain length, and more specifically, a polynucleotide fragment encoding the modified polypeptide.

Specifically, due to codon degeneracy or in consideration of the codons preferred in an organism in which the polypeptide is to be expressed, the polynucleotide of the present disclosure may undergo various modifications in the coding region within the scope that does not change the amino acid sequence of the polypeptide. Specifically, any polynucleotide sequence encoding the NADP-dependent glyceraldehyde-3-phosphate dehydrogenase including the amino acid sequence of SEQ ID NO: 1 may be included without limitation.

Additionally, a probe that may be prepared from a known gene sequence, for example, any sequence which can hybridize with a sequence complementary to all or part of the nucleotide sequence under stringent conditions to encode a polypeptide having the activity of NADP-dependent glyceraldehyde-3-phosphate dehydrogenase including the amino acid sequence of SEQ ID NO: 1 may be included without limitation. The "stringent conditions" refer to conditions under which specific hybridization between polynucleotides is allowed. Such conditions are specifically described in the literature (see J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8). For example, the stringent conditions may include conditions under which genes having a high homology or identity of 40% or higher, specifically 90% or higher, more specifically 95% or higher, much more specifically 97% or higher, and still much more specifically 99% or higher are hybridized with each other and genes having a homology or identity lower than the above homologies or identities are not hybridized with each other, or washing conditions of Southern hybridization, that is, washing once, specifically, twice or three times at a salt concentration and a temperature corresponding to 60° C., 1×SSC, and 0.1% SDS; specifically, 60° C., 0.1×SSC, and 0.1% SDS; and more specifically 68° C., 0.1×SSC, and 0.1% SDS.

Hybridization requires that two nucleic acids contain complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the present disclosure may include isolated nucleotide fragments complementary to the entire sequence as well as nucleic acid sequences substantially similar thereto.

Specifically, the polynucleotides having a homology or identity may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

The appropriate stringency for hybridizing polynucleotides depends on the length of the polynucleotides and the degree of complementation, and these variables are well known in the art (see Sambrook et al.).

As used herein, the term "homology" or "identity" refers to a degree of relevance between two given amino acid sequences or nucleotide sequences, and may be expressed as a percentage. The terms "homology" and "identity" may often be used interchangeably with each other.

The sequence homology or identity of conserved polynucleotide or polypeptide sequences may be determined by standard alignment algorithms and can be used with a default gap penalty established by the program being used. Substantially homologous or identical sequences are generally expected to hybridize to all or at least about 50%, 60%, 70%, 80%. or 90% of the entire length of the sequences under moderate or highly stringent conditions. Polynucleotides that contain degenerate codons instead of codons in hybridizing polynucleotides are also considered.

Whether any two polynucleotide sequences have a homology, similarity, or identity may be determined, for example, by a known computer algorithm such as the "FASTA" program (Pearson et al, (1988) Proc. Natl. Acad. Sci. USA 85: 2444) using default parameters. Alternatively, it may be determined by the Needleman-Wunsch algorithm (Needleman and Wunsch, 1970, J. Mol. Biol. 48: 443-453), which is performed using the Needleman program of the EMBOSS package (EMBOSS: The European Molecular Biology Open Software Suite, Rice et al., 2000, Trends Genet. 16: 276-277) (preferably, version 5.0.0 or versions thereafter) (GCG program package (Devereux, J., et al., Nucleic Acids Research 12: 387 (1984)), BLASTP, BLASTN, FASTA (Atschul, S. F., et al., J MOLEC BIOL 215: 403 (1990); Guide to Huge Computers, Martin J. Bishop, ed., Academic Press, San Diego, 1994, and CARILLO et al. (1988) SIAM J Applied Math 48: 1073). For example, the homology, similarity, or identity may be determined using BLAST or ClustalW of the National Center for Biotechnology Information (NCBI).

The homology, similarity, or identity of polynucleotides or polypeptides may be determined by comparing sequence information using, for example, the GAP computer program, such as Needleman et al. (1970), J Mol Biol. 48: 443 as disclosed in Smith and Waterman, Adv. Appl. Math (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), Nucl. Acids Res. 14:6745, as disclosed in Schwartz and Dayhoff, eds., Atlas of Protein Sequence and Structure, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity, or identity with each other may be identified by comparing the sequences in a Southern hybridization experiment under stringent conditions as defined, and appropriate hybridization conditions defined are within the skill of the art, and may be determined by a method well known to those skilled in the art (for example, J. Sambrook et al., Molecular Cloning, A Laboratory Manual, $2^{nd}$ Edition, Cold Spring Harbor Laboratory press, Cold Spring Harbor, New York, 1989; F. M. Ausubel et al., Current Protocols in Molecular Biology, John Wiley & Sons, Inc., New York).

The gene encoding the NADP-dependent glyceraldehyde-3-phosphate dehydrogenase may be introduced into the microorganism of the genus Corynebacterium by a conventional method known in the art, and the NADP-dependent glyceraldehyde-3-phosphate dehydrogenase may be expressed in the microorganism of the genus Corynebacterium.

As used herein, the term "to be expressed/being expressed" refers to a state in which a target polypeptide is introduced into a microorganism or in which a target polypeptide is modified to be expressed in the microorganism. For the purpose of the present disclosure, the "target polypeptide" may be the NADP-dependent glyceraldehyde-3-phosphate dehydrogenase described above.

Specifically, as used herein, the term "introduction of a polypeptide" means that a microorganism exhibits the activity of a target polypeptide which was not originally possessed by the microorganism. For example, it may mean that a polynucleotide encoding the target polypeptide is introduced into the chromosome of the microorganism, or a vector containing the polynucleotide encoding the target polypeptide is introduced into the microorganism and thereby exhibits its activity. Even if the target polypeptide is already present in the microorganism, the expression or activity of the polypeptide in the microorganism may be increased or enhanced compared to that of a non-modified microorganism due to the introduction of the target polypeptide into the microorganism.

Additionally, as used herein, the term "enhancement of activity" means that the activity of a particular protein in a microorganism is enhanced compared to its endogenous activity or the activity of a polypeptide in a non-modified microorganism. As used herein, the term "endogenous activity" refers to the activity of a particular protein originally possessed by a parent strain before transformation, when a trait of a microorganism is altered due to genetic modification caused by a natural or artificial factor.

Specifically, the enhancement of activity may be achieved by one or more of the following methods selected from the group consisting of: a method of introducing the polypeptide into the microorganism, a method of increasing the intracellular copy number of a gene encoding the polypeptide; a method of introducing modification into the expression control sequence of a gene encoding the polypeptide; a method of replacing the expression control sequence of a gene encoding the polypeptide with a sequence having strong activity, and a method of further introducing modification into a gene encoding the polypeptide such that the activity of the polypeptide is enhanced, but is not limited thereto.

In the above, the method of introducing the polypeptide into the microorganism or the method of increasing the intracellular copy number of a gene may be performed by inserting a polynucleotide encoding the polypeptide into the chromosome or plasmid of the microorganism using a vector, but is not particularly limited thereto. Specifically, the method may be performed by introducing a vector which is operably linked to the polynucleotide encoding the polypeptide of the present disclosure and is able to replicate and function regardless of the host cell. Alternatively, the method may be performed by introducing a vector, which is able to insert the polynucleotide into the chromosome of a host cell and is operably linked to the polynucleotide, into the chromosome of a host cell. The insertion of the polynucleotide into the chromosome may be achieved by a method known in the art, for example, by homologous recombination.

Next, the modification of the expression control sequence so as to increase the expression of the polynucleotide may be performed by inducing a modification on the sequence through deletion, insertion, non-conservative or conservative substitution of the nucleotide sequence, or a combination thereof to further enhance the activity of the expression control sequence, or by replacing the polynucleotide sequence with a nucleic acid sequence having a stronger activity, but is not particularly limited thereto. The expression control sequence may include, but is not particularly limited to, a promoter, an operator sequence, a sequence encoding a ribosome-binding site, and a sequence regulating the termination of transcription and translation.

Specifically, a strong promoter, instead of the original promoter, may be connected to the upstream region of the expression unit of the polynucleotide. Examples of the strong promoter may include cj1 to cj7 promoters (Korean Patent No. 10-0620092), lac promoter, trp promoter, trc promoter, tac promoter, lambda phage PR promoter, PL promoter, tet promoter, gapA promoter, SPL7 promoter, SPL13 (sm3) promoter (Korean Patent No. 10-1783170), O2 promoter (Korean Patent No. 10-1632642), tkt promoter, and yccA promoter, but is not limited thereto.

Furthermore, although not particularly limited thereto, the modification of the polynucleotide sequence on the chromosome may be performed by inducing a modification on the expression control sequence through deletion, insertion, non-conservative or conservative substitution of the nucleic acid sequence, or a combination thereof to further enhance the activity of the polynucleotide sequence, or by replacing the polynucleotide sequence with a polynucleotide sequence modified to have a stronger activity.

The introduction and enhancement of the polypeptide activity may be an increase in the activity or concentration of the corresponding polypeptide compared to the activity or concentration of the polypeptide in a wild-type or non-modified microbial strain, but is not limited thereto.

Specifically, the introduction or enhancement of the activity of NADP-dependent glyceraldehyde-3-phosphate dehydrogenase may be achieved by preparing a recombinant vector for expression containing a gene encoding the same, and introducing the vector into the microorganism of the genus *Corynebacterium* to produce a transformed microorganism of the genus *Corynebacterium*. That is, the microorganism containing the gene encoding the NADP-dependent glyceraldehyde-3-phosphate dehydrogenase may be a recombinant microorganism produced by transforming into a vector containing the gene, but is not limited thereto.

As used herein, the term "vector" refers to a DNA product containing an appropriate control sequence and a nucleotide sequence of a target polypeptide to express the target polypeptide in a suitable host. The control sequence may include a promoter capable of initiating transcription, an arbitrary operator sequence for controlling transcription, a sequence encoding an appropriate mRNA ribosome-binding site, and sequences for controlling the termination of transcription and translation. Once transformed into a suitable host cell, the vector may replicate or function independently of the host genome or may be integrated into the genome itself.

The vector used in the present disclosure is not particularly limited as long as it is able to replicate in the host cell, and any vector known in the art may be used. Examples of the vector conventionally used may include natural or recombinant plasmids, cosmids, viruses, and bacteriophages. For example, as a phage vector or cosmid vector, pWE15, M13, λEMBL3, λEMBL4, λFIXII, λDASHII, λZAPII, λgt10, λgt11, MBL3, MBL4, IXII, ASHII, APII, t10, t11, Charon4A, and Charon21A may be used; and as a plasmid vector, those based on pBR, pUC, pBluescriptll, pGEM, pTZ, pET, pMal, pQE, and pCL may be used. Specifically, pDZ, pACYC177, pACYC184, pCL, pECCG117, pUC19, pBR322, pMW118, and pCC1 BAC vectors may be used.

The recombinant vector for expression of NADP-dependent glyceraldehyde-3-phosphate dehydrogenase may be prepared by a conventional method. That is, it may be prepared by ligating the gene sequence of the NADP-dependent glyceraldehyde-3-phosphate dehydrogenase to an appropriate vector using a restriction enzyme.

A polynucleotide encoding a target polypeptide may be inserted into the chromosome using a recombinant vector for polypeptide expression. The insertion of the polynucleotide into the chromosome may be performed by any method known in the art, for example, by homologous recombination, but the method is not limited thereto. Additionally, the vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface polypeptides, may be used. Under the circumstances of being treated with a selective agent, only the cells expressing the selection marker can survive or express other phenotypic traits, and thus the transformed cells can be selected.

As used herein, the term "transformation" refers to the introduction of a vector including a polynucleotide encoding a target polypeptide into a host cell so that the polypeptide encoded by the polynucleotide can be expressed in a host cell. As long as the transformed polynucleotide can be expressed in the host cell, it does not matter whether the transformed polynucleotide is integrated into the chromosome of the host cell and located therein or located extrachromosomally, and both cases can be included. Further, the polynucleotide may include DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. The expression cassette may commonly include a promoter operably linked to the polynucleotide, a transcription terminator, a ribosome-binding site, or a translation terminator. The expression cassette may be in the form of a self-replicable expression vector. Additionally, the polynucleotide may be introduced into the host cell as it is and operably linked to sequences required for expression in the host cell, but is not limited thereto.

In addition, as used herein, the term "operably linked" means that the gene sequence is functionally linked to a promoter sequence that initiates and mediates transcription of the polynucleotide encoding the target polypeptide of the present disclosure.

The method of transforming the vector of the present disclosure includes any method of introducing a nucleic acid into a cell, and may be performed by selecting a suitable standard technique known in the art, depending on the host cell. For example, the method may include electroporation, calcium phosphate ($CaPO_4$) precipitation, calcium chloride (CaCl$_2$) precipitation, microinjection, a polyethyleneglycol (PEG) method, a DEAE-dextran method, a cationic liposome method, and a lithium acetate-DMSO method, but is not limited thereto.

For the purposes of the present disclosure, the microorganism of the genus *Corynebacterium*, which is genetically modified to express the NADP-dependent glyceraldehyde-3-phosphate dehydrogenase including the amino acid sequence of SEQ ID NO: 1, may be a microorganism with an increased L-amino acid producing ability compared to a non-modified microorganism.

As used herein, the term "L-amino acid-producing microorganism" or "L-amino acid-producing microorganism of the *Corynebacterium*" includes all of microorganisms or microorganisms of the genus *Corynebacterium* in which a natural or artificial genetic modification occurs, and it may refer to a microorganism of the genus *Corynebacterium* in which a genetic mutation occurs or in which activity is enhanced for the production of desired L-amino acids as a microorganism having a particular weakened or enhanced mechanism due to insertion of a foreign gene, or enhancement or inactivation of activity of an endogenous gene.

Specifically, the L-amino acid-producing microorganism may be a microorganism in which the desired L-amino acid producing ability is enhanced due to enhancement of activity of the part of polypeptides involved in the desired L-amino acid biosynthesis pathway or weakening of activity of the part of polypeptides involved in the desired L-amino acid degradation pathway. For example, the microorganism may be a microorganism in which the activity of aspartate kinase (lysC), homoserine dehydrogenase (hom), L-threonine dehydratase (ilvA), 2-isopropylmalate synthase (leuA), acetolactate synthase (ilvN), or/and homoserine O-acetyltransferase (metX) is enhanced. Additionally, the microorganism may include, for example, a gene or a polypeptide which is modified to have resistance to feedback inhibition so as to enhance activity. Further, the microorganism may, for example, have a weakened or inactivated activity of various genes or polypeptides that degrade desired L-amino acids. In addition, the microorganism may be, for example, a microorganism having an increased L-amino acid producing ability due to random mutation, but is not limited thereto. That is, the microorganism may be a microorganism in which the production of desired L-amino acids is increased by enhancing the polypeptide activity involved in the desired L-amino acid biosynthetic pathway or by inactivating/weakening the polypeptide activity involved in the degradation pathway.

As described above, the enhancement of the polypeptide activity may be achieved by increasing the intracellular copy number of the genes encoding the polypeptide; by introducing a mutation into a chromosomal gene encoding the polypeptide and/or its expression control sequence; by replacing the gene expression control sequence on the chromosome encoding the polypeptide with a sequence having strong activity; by introducing a mutation into a part of the gene on the chromosome encoding the polypeptide to increase the expression of the polypeptide or to have resistance to feedback inhibition; or a combination thereof, but is not limited thereto.

As used herein, the term "weakening/inactivation of polypeptide activity" means that a natural wild-type strain, a parent strain, or the corresponding polypeptide have no expression of the enzyme or polypeptide, or have no activity or decreased activity even though expressed, as compared to a non-modified strain. Here, the decrease is a comprehensive concept including the case where the polypeptide activity itself is decreased compared to the activity of the polypeptide originally possessed by a microorganism due to the mutation of the gene encoding the polypeptide, modification of the expression control sequence, or deletion in a part or all of the genes, etc.; the case where the overall level of intracellular polypeptide activity is decreased compared to that of a natural strain or a strain before modification due to the inhibition of expression of the gene encoding the polypeptide or the inhibition of translation; and a combination thereof. In the present disclosure, the inactivation may be achieved by applying various methods well known in the art. Examples of the methods may include a method for deleting a part or all of the gene encoding the polypeptide; a method for modifying the expression control sequence such that the expression of the gene is decreased; a method for modifying the gene sequence encoding the polypeptide such that the polypeptide activity is removed or weakened; a method for introducing an antisense oligonucleotide (for example, antisense RNA) that binds complementarily to the transcript of the gene encoding the polypeptide; a method for incorporating a complementary sequence to the Shine-Dalgarno sequence upstream of the Shine-Dalgarno sequence of the gene encoding the polypeptide to form a secondary structure, thereby inhibiting the ribosomal attachment; and a reverse transcription engineering (RTE) method for incorporating a promoter at the 3' terminus of an open reading frame (ORF) of the polynucleotide sequence of the gene encoding the polypeptide so as to be reversely transcribed; and a combination thereof.

However, as an example of the above-described method, a method for enhancing or inactivating the activity of a polypeptide and a method for genetic manipulation are known in the art, and the L-amino acid-producing microorganism can be prepared by applying various known methods.

For the purpose of the present disclosure, the L-amino acid-producing microorganism of the genus *Corynebacterium* containing the NADP-dependent glyceraldehyde-3-phosphate dehydrogenase can produce the desired L-amino acids in excess from a carbon source in the medium, as compared to a non-modified wild-type strain or a non-modified mutant, as described above. In the present disclosure, the "L-amino acid-producing microorganism of the genus *Corynebacterium*" can be used interchangeably with "a strain of the genus *Corynebacterium* having an L-amino acid producing ability" or "an L-amino acid-producing strain of the genus *Corynebacterium*".

The L-amino acid-producing microorganism of the genus *Corynebacterium*, which is modified to express the polypeptide having the activity of NADP-dependent glyceraldehyde-3-phosphate dehydrogenase, is not limited as long as it is a microorganism of the genus *Corynebacterium* that can produce L-amino acids. Specifically, the microorganism of the genus *Corynebacterium* may be any one or more selected from the group consisting of *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, and *Corynebacterium flavescens*, and specifically, it may be *Corynebacterium glutamicum*, but is not limited thereto.

The L-amino acid-producing microorganism of the genus *Corynebacterium* may be a recombinant microorganism. The recombinant microorganism is as described above.

As used herein, the term "cultivation" means that the microorganism is grown under appropriately controlled environmental conditions. The cultivation process of the present disclosure can be performed in a suitable culture medium and under culture conditions known in the art. Such a cultivation process may be easily adjusted for use by those skilled in the art according to the strain to be selected. Specifically, the cultivation may be a batch culture, a continuous culture, and a fed-batch culture, but is not limited thereto.

As used herein, the term "medium" refers to a mixture of materials which contains nutrient materials required for the cultivation of the microorganism as a main ingredient, and it supplies nutrient materials and growth factors, along with water that is essential for survival and growth. Specifically, the medium and other culture conditions used for culturing the microorganism of the present disclosure may be any medium used for conventional cultivation of microorganisms without any particular limitation. However, the microorganism of the present disclosure may be cultured under aerobic conditions in a conventional medium containing an appropriate carbon source, nitrogen source, phosphorus source, inorganic compound, amino acid, and/or vitamin, while adjusting temperature, pH, etc. Specifically, the culture medium for the strains of the genus *Corynebacterium* can be found in the literature ("Manual of Methods for General Bacteriology" by the American Society for Bacteriology (Washington D.C., USA, 1981)).

In the present disclosure, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; and amino acids, such as glutamic acid, methionine, lysine, etc. Additionally, the carbon source may include natural organic nutrients such as starch hydrolysate, molasses, blackstrap molasses, rice bran, cassava, sugar cane molasses, corn steep liquor, etc. Specifically, carbohydrates such as glucose and sterilized pretreated molasses (i.e., molasses converted to reducing sugar) may be used, and in addition, various other carbon sources in an appropriate amount may be used without limitation. These carbon sources may be used alone or in a combination of two or more kinds, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more kinds, but are not limited thereto.

The phosphorus source may include monopotassium phosphate, dipotassium phosphate, or corresponding sodium-containing salts, etc. Examples of the inorganic compound may include sodium chloride, calcium chloride, iron chloride, magnesium sulfate, iron sulfate, manganese sulfate, calcium carbonate, etc. Additionally, amino acids, vitamins, and/or appropriate precursors may be included. These constituting ingredients or precursors may be added to a medium in a batch culture or continuous manner, but these phosphorus sources are not limited thereto.

In the present disclosure, the pH of a medium may be adjusted during the cultivation of a microorganism by adding a compound such as ammonium hydroxide, potassium hydroxide, ammonia, phosphoric acid, sulfuric acid, etc. to the medium in an appropriate manner. Additionally, during the cultivation, an antifoaming agent such as fatty acid polyglycol ester may be added to prevent foam generation. In addition, oxygen or oxygen-containing gas may be injected into the medium in order to maintain an aerobic state of the medium; or nitrogen, hydrogen, or carbon dioxide gas may be injected without the injection of gas in order to maintain an anaerobic or microaerobic state of the medium, but the gas is not limited thereto.

The medium temperature may be in a range from 20° C. to 45° C., and specifically, from 25° C. to 40° C., but is not limited thereto. The cultivation may be continued until the useful materials are obtained in desired amounts, and specifically for 10 to 160 hours, but is not limited thereto.

The L-amino acids produced by the cultivation may be released into the medium or may not be released and remain in the cells.

In the method of recovering L-amino acids produced in the culturing of the present disclosure, the desired L-amino acids may be collected from the culture solution using appropriate methods known in the art depending on the cultivation method. For example, methods such as centrifugation, filtration, ion exchange chromatography, crystallization, and HPLC may be used, and the desired L-amino acids may be recovered from the medium or microorganism using a suitable method known in the art.

Further, the recovering may further include a purification process, which may be performed using an appropriate method known in the art. Thus, the recovered L-amino acids may be in a purified state or in a microbial fermentation broth containing the L-amino acids (Introduction to Biotechnology and Genetic Engineering, A. J. Nair., 2008).

The L-amino acids produced from the method for producing L-amino acids according to the present disclosure are not limited by type. That is, the L-amino acids that can be produced from the microorganisms of the genus *Corynebacterium* may include any L-amino acid without limitation, and intermediates of the L-amino acids may also be included. The L-amino acids may be, for example, L-arginine, L-histidine, L-lysine, L-aspartic acid, L-glutamic acid, L-serine, L-threonine, L-asparagine, L-glutamine, L-tyrosine, L-alanine, L-isoleucine, L-leucine, L-valine, L-phenylalanine, L-methionine, L-tryptophan, glycine, L-proline, and L-cysteine, and specifically, may be L-lysine, L-threonine, L-isoleucine, L-leucine, L-valine, L-arginine, and L-glutamic acid, but are not limited thereto. The intermediate of the L-amino acids may be, for example, O-acetyl homoserine, but is not limited thereto.

Another aspect of the present disclosure is to provide a microorganism of the genus *Corynebacterium* having an increased L-amino acid producing ability, containing NADP-dependent glyceraldehyde-3-phosphate dehydrogenase, which includes an amino acid sequence of SEQ ID NO: 1.

The NADP-dependent glyceraldehyde-3-phosphate dehydrogenase, the gene encoding the same, the expression thereof, and the microorganism of the genus *Corynebacterium* are as described above.

In the present disclosure, the microorganism of the genus *Corynebacterium* containing the gene encoding the NADP-dependent glyceraldehyde-3-phosphate dehydrogenase may have an increased or improved L-amino acid producing ability as compared to a non-modified microorganism due to the expression of the NADP-dependent glyceraldehyde-3-phosphate dehydrogenase.

The microorganism of the genus *Corynebacterium* of the present disclosure is a microorganism capable of producing L-amino acids, and may include not only wild-type microorganisms, but also microorganisms genetically modified to improve the L-amino acid producing ability. The L-amino acid-producing microorganism is as described above.

The microorganism of the present disclosure is a recombinant microorganism containing the NADP-dependent glyceraldehyde-3-phosphate dehydrogenase derived from the genus *Lactobacillus*, and can produce the desired L-amino acids in excess from the carbon source in the medium as compared to a microorganism not containing the NADP-dependent glyceraldehyde-3-phosphate dehydrogenase. The increased L-amino acid producing ability of the recombinant microorganism may be obtained with an increased reducing power by activation of the NADP-dependent glyceraldehyde-3-phosphate dehydrogenase. That is, by introducing the NADP-dependent glyceraldehyde-3-phosphate dehydrogenase into the microorganism of the genus *Corynebacterium* that produces L-amino acids, the NADP-dependent glyceraldehyde-3-phosphate dehydrogenase is activated such that NADP can be used instead of NAD as a coenzyme, and accordingly, the amount of NADPH can be increased, which then can be used for reducing power as an energy source in the biosynthesis of L-amino acids.

In the present disclosure, the term "non-modified microorganism" may refer to a natural strain itself, a microorganism not containing the NADP-dependent glyceraldehyde-3-phosphate dehydrogenase, or a microorganism that has not been transformed with a vector containing a polynucleotide encoding the NADP-dependent glyceraldehyde-3-phosphate dehydrogenase, but is not limited thereto.

The L-amino acid is as described above.

The microorganism of the genus *Corynebacterium* in which the L-amino acid producing ability is increased by introducing the gene encoding the NADP-dependent glyceraldehyde-3-phosphate dehydrogenase according to the present disclosure may be any one selected from the group consisting of the microorganisms of the genus *Corynebacterium* deposited with Accession No. KCCM12580P, Accession No. KCCM12581P, Accession No. KCCM12582P, Accession No. KCCM12583P, Accession No. KCCM12584P, Accession No. KCCM12585P, Accession No. KCCM12586P, or Accession No. KCCM12587P.

Still another aspect of the present disclosure is to provide the use of L-amino acid production of a microorganism of the genus *Corynebacterium* containing NADP-dependent glyceraldehyde-3-phosphate dehydrogenase, which includes an amino acid sequence of SEQ ID NO: 1.

The NADP-dependent glyceraldehyde-3-phosphate dehydrogenase, the gene encoding the same, the expression thereof, the microorganism of the genus *Corynebacterium*, the microorganism of the genus *Corynebacterium* containing the NADP-dependent glyceraldehyde-3-phosphate dehydrogenase, which includes the amino acid sequence of SEQ ID NO: 1, and the L-amino acid are as described above.

MODE FOR CARRYING OUT THE INVENTION

Hereinafter, the present disclosure will be described in detail by way of Examples. However, it will be apparent to those skilled in the art to which the present disclosure belongs that these Examples are provided for illustrative purposes only, and the scope of the invention is not intended to be limited thereto.

Example 1-1. Preparation of Vector for Introducing *Lactobacillus delbrueckii* subsp. *bulgaricus* ATCC11842-Derived NADP-Dependent Glyceraldehyde-3-Phosphate Dehydrogenase (gapN(L)) into Transposon on Chromosome of Microorganism of Genus *Corynebacterium*

*Lactobacillus delbrueckii* subsp. *bulgaricus*-derived NADP-dependent glyceraldehyde-3-phosphate dehydrogenase was selected as NADP-dependent glyceraldehyde-3-phosphate dehydrogenase with a high affinity for *Corynebacterium*. Thereafter, the following experiment was performed to enhance its activity.

An amino acid sequence (SEQ ID NO: 1) and a nucleotide sequence (SEQ ID NO: 2) of the Ldb1179 gene encoding the *Lactobacillus delbrueckii* subsp. *bulgaricus* ATCC11842-derived gapN were obtained from NIH GenBank.

Further, in order to introduce the Ldb1179 gene into the chromosome using a transposon gene region of a microorganism of the genus *Corynebacterium*, four types of vectors for transformation were each prepared, and cj7 (Korean Patent No. 10-0620092) was used as a promoter.

1-1-1) Preparation of pDZ2457::P(cj7)-gapN(L) Vector

The Ldb1179 gene was amplified as a gene fragment of about 1.43 kb using primers of SEQ ID NOS: 3 and 4 based on the chromosome of *Lactobacillus delbrueckii* subsp. *bulgaricus* ATCC11842 strain as a template by modifying the start codon TTG to ATG (Table 1). At this time, PCR was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of about 1.4 kb was eluted and purified. Further, PCR was performed on the cj7 promoter region using a pair of primers of SEQ ID NOS: 5 and 6 under the same conditions to obtain a PCR product. At this time, the PCR was performed by repeating 30 cycles of denaturation at 95° C. for 30 seconds, annealing at 55° C. for 30 seconds, and extension at 72° C. for 30 seconds. The PCR product obtained above was subjected to fusion cloning. The fusion cloning was performed using an In-Fusion® HD cloning kit (Clontech). The resulting plasmid was named pDZ2457::P (cj7)-gapN(L).

The vector was used to introduce the gapN into lysine-, leucine-, or acetyl homoserine-producing strains.

1-1-2) Preparation of pDZ1108::P(cj7)-gapN(L) Vector

The Ldb1179 gene was amplified as a gene fragment of about 1.43 kb using primers of SEQ ID NOS: 3 and 7 based on the chromosome of *Lactobacillus delbrueckii* subsp. *bulgaricus* ATCC11842 strain as a template by modifying the start codon TTG to ATG (Table 1). At this time, PCR was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of about 1.4 kb was eluted and purified. Further, PCR was performed on the cj7 promoter region using a pair of primers of SEQ ID NOS: 8 and 6 under the same conditions to obtain a PCR product. At this time, the PCR was performed by repeating 30 cycles of denaturation at 95° C. for 30 seconds, annealing at 55° C. for 30 seconds, and extension at 72° C. for 30 seconds. The PCR product obtained above was subjected to fusion cloning. The fusion cloning was performed using an In-Fusion® HD cloning kit (Clontech). The resulting plasmid was named pDZ1108::P(cj7)-gapN(L).

The vector was used to introduce the gapN into isoleucine- or threonine-producing strains.

1-1-3) Preparation of pDZTn5::P(cj7)-gapN(L) Vector

The Ldb1179 gene was amplified as a gene fragment of about 1.43 kb using primers of SEQ ID NOS: 3 and 10 based on the chromosome of *Lactobacillus delbrueckii* subsp. *bulgaricus* ATCC11842 strain as a template by modifying the start codon TTG to ATG (Table 1). At this time, PCR was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of about 1.4 kb was eluted and purified. Further, PCR was performed on the cj7 promoter region using a pair of primers of SEQ ID NOS: 9 and 6 under the same conditions to obtain a PCR product. At this time, the PCR was performed by repeating 30 cycles of denaturation at 95° C. for 30 seconds, annealing at 55° C. for 30 seconds, and extension at 72° C. for 30 seconds. The PCR product obtained above was subjected to fusion cloning. The fusion cloning was performed using an In-Fusion® HD cloning kit (Clontech). The resulting plasmid was named pDZTn5::P(cj7)-gapN(L).

The vector was used to introduce the gapN into valine- or arginine-producing strains.

1-1-4) Preparation of pDZ0286::P(cj7)-gapN(L) Vector

The Ldb1179 gene was amplified as a gene fragment of about 1.43 kb using primers of SEQ ID NOS: 3 and 12 based on the chromosome of *Lactobacillus delbrueckii* subsp. *bulgaricus* ATCC11842 strain as a template by modifying the start codon TTG to ATG (Table 1). At this time, PCR was performed by repeating 30 cycles of denaturation at 95° C. for 30 seconds, annealing at 55° C. for 30 seconds, and extension at 72° C. for 1 minute and 30 seconds. This PCR product was subjected to electrophoresis in a 0.8% agarose gel, and a band of about 1.4 kb was eluted and purified. Further, PCR was performed on the cj7 promoter region using a pair of primers of SEQ ID NOS: 11 and 6 under the same conditions to obtain a PCR product. At this time, PCR was performed by repeating 30 cycles of denaturation at 95° C. for 30 seconds, annealing at 55° C. for 30 seconds, and extension at 72° C. for 30 seconds. The PCR product obtained above was subjected to fusion cloning. The fusion cloning was performed using an In-Fusion® HD cloning kit (Clontech). The resulting plasmid was named pDZ0286::P(cj7)-gapN(L).

The vector was used to introduce the gapN into glutamic acid-producing strains.

TABLE 1

| SEQ ID NO: | Sequence (5'-3') |
|---|---|
| 3 | CCCAACGAAAGGAAACACTCATGACAGAACACTATTTAAA |
| 4 | GCTTGTGAATAAGCCTGCCCTTAGTCTTCGATGTTGAAGACAACG |
| 5 | GATTCCAGGTTCCTTAACCCAGAAACATCCCAGCGCTACT |
| 6 | TTTAAATAGTGTTCTGTCATGAGTGTTTCCTTTCGTTGGG |
| 7 | TTTCGTGCGAGTCTAGAAGTTTAGTCTTCGATGTTGAAGA |
| 8 | ACGAGGTCAGCATCTCGAGTAGAAACATCCCAGCGCTACT |
| 9 | CGCGGAACTGTACTAGTAGAAACATCCCAGCGCTAC |
| 10 | GGAAGGATATCTCTAGAAGATAAAACGAAAGGCC |
| 11 | CCCTTCCGGTTTAGTACTAGAAACATCCCAGCGCTA |
| 12 | CTCTTCCTGTTTAGTACTTTAGTCTTCGATGTTGAAG |

Example 1-2. Preparation of Vector for Introducing *Streptococcus mutans* ATCC25175-Derived NADP-Dependent Glyceraldehyde-3-Phosphate Dehydrogenase (gapN(S)) into Transposon on Chromosome of Microorganism of Genus *Corynebacterium*

As a control group of the *Lactobacillus delbrueckii* subsp. *bulgaricus* ATCC11842-derived gapN, the following experiment was performed in order to introduce SMUFR 0590 (Korean Patent No. 10-1182033) having the activity of NADP-dependent glyceraldehyde-3-phosphate dehydrogenase into the *Streptococcus mutans* ATCC25175.

An amino acid sequence (SEQ ID NO: 13) and a nucleotide sequence (SEQ ID NO: 14) of the SMUFR 0590 gene encoding the *Streptococcus mutans* ATCC25175-derived gapN were obtained from NIH GenBank, and a vector for introducing SMUFR 0590 expressed by cj7 promoter into the transposon gene was prepared.

As in Example 1-1, pDZ was used as a vector for transformation, and cj7 was used as a promoter. The *Streptococcus mutans* ATCC25175-derived SMUFR 0590 gene was amplified as a gene fragment of about 1.7 kb based on the pECCG122-Pcj7-gapN (Korean Patent No. 10-1182033) as a template using primers of SEQ ID NOS: 15 and 16 (Table 2). At this time, PCR was performed by repeating 30 cycles of denaturation at 95° C. for 30 seconds, annealing at 55° C. for 30 seconds, and extension at 72° C. for 2 minutes. This PCR product was subjected to electrophoresis in a 0.8% agarose gel, and a band of a desired size was eluted and purified. The PCR product obtained above was subjected to fusion cloning. The fusion cloning was performed using an In-Fusion® HD cloning kit (Clontech). The resulting plasmid was named pDZTn::P(cj7)-gapN(S).

TABLE 2

| SEQ ID NO: | Sequence (5'-3') |
|---|---|
| 15 | TAGATGTCGGGCCCCATATGAGAAACATCCCAGCGCTACT |
| 16 | GCCAAAACAGCCTCGAGTTATTTGATATCAAATACGACGGATTTA |

Example 1-3. Preparation of Vector for Introducing Clostridium acetobutylicum-Derived NADP-Dependent Glyceraldehyde-3-Phosphate Dehydrogenase (gapN(C)) into Transposon on Chromosome of Microorganism of Genus Corynebacterium As a control group of the *Lactobacillus delbrueckii* subsp. *bulgaricus* ATCC11842-derived gapN, the following experiment was performed in order to introduce the gapN of NCBI GenBank WP_010966919.1 having the activity of NADP-dependent glyceraldehyde-3-phosphate dehydrogenase activity into *Clostridium acetobutylicum*.

An amino acid sequence (SEQ ID NO: 35) and a nucleotide sequence (SEQ ID NO: 36) of the gapN gene of *Clostridium acetobutylicum*-derived NCBI GenBank WP_010966919.1 and NCBI GenBank NC_015687.1 were obtained from NCBI GenBank, and a vector for introducing the gapN of NCBI GenBank WP_010966919.1 expressed by cj7 promoter into the transposon gene was prepared.

As in Example 1-1, pDZ was used as a vector for transformation and cj7 was used as a promoter. The gapN gene of *Clostridium acetobutylicum*-derived NCBI GenBank WP_010966919.1 was amplified as a gene fragment of about 1.5 kb based on the gDNA of *Clostridium acetobutylicum* as a template using primers of SEQ ID NOS: 37 and 38. Additionally, in order to obtain the cj7 promoter, the gapN gene was amplified as a gene fragment of about 400 bp based on the pECCG122-Pcj7-gapN (Korean Patent No. 10-1182033) as a template using primers of SEQ ID NOS: 15 and 39. At this time, PCR was performed by repeating 30 cycles of denaturation at 95° C. for 30 seconds, annealing at 55° C. for 30 seconds, and extension at 72° C. for 2 minutes. This PCR product was subjected to electrophoresis in a 0.8% agarose gel, and a band of a desired size was eluted and purified. The PCR product obtained above was subjected to fusion cloning. The fusion cloning was performed using an In-Fusion® HD cloning kit (Clontech). The resulting plasmid was named pDZTn::P(cj7)-gapN(C).

TABLE 3

| SEQ ID NO: | Sequence (5'-3') |
|---|---|
| 37 | ACCCAACGAAAGGAAACACTCATGTTTGAAAATATATCATCAAA |
| 38 | GCCAAAACAGCCTCGAGTTATAGGTTTAAAACTATTGATT |
| 39 | TTTGATGATATATTTTCAAACATGAGTGTTTCCTTTCGTTGGGT |

Example 2-1. Preparation of Strains Introduced with gapN(L), gapN(S), or gapN(C) in L-Lysine-Producing Strain KCCM11016P and Evaluation Thereof In order to confirm the effect of introducing the gapN derived from *L. delbrueckii* subsp. *bulgaricus* or *S. mutans* on the L-lysine producing ability based on the *Corynebacterium glutamicum* ATCC13032 strain, the plasmid prepared in Example 1-1-1, the plasmid prepared in Example 1-2, and the plasmid prepared in Example 1-3 were introduced into *Corynebacterium glutamicum* KCCM11016P (Korean Patent No. 10-0159812) by electroporation to obtain transformants, and the transformants were spread on a BHIS plate medium (37 g/L of Brain heart infusion, 91 g/L of sorbitol, 2% agar) containing kanamycin (25 µg/mL) and X-gal (5-bromo-4-chloro-3-indolyl-β-D-galactoside), and cultured to form colonies. From the colonies thus formed, blue colonies were selected so as to select strains introduced with the P(cj7)-gapN(L), P(cj7)-gapN(S), or P(cj7)-gapN(C).

The thus-selected strains were named KCCM11016P:::P(cj7)-gapN(L), KCCM11016P::P(cj7)-gapN(S), and KCCM11016P:::P(cj7)-gapN(C), respectively.

The prepared strains were cultured in the following manner to compare the lysine producing ability. Each strain was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of a production medium, and cultured at 32° C. for 72 hours at 200 rpm with shaking. Compositions of the seed medium and production medium are shown below.

<Seed Medium (pH 7.0)>
Glucose 20 g, Peptone 10 g, Yeast Extract 5 g, Urea 1.5 g, $KH_2PO_4$ 4 g, $K_2HPO_4$ 8 g, $MgSO_4 \cdot 7H_2O$ 0.5 g, Biotin 100 µg, Thiamine-HCl 1000 µg, Calcium-Pantothenic Acid 2000 µg, Nicotinamide 2000 µg (based on 1 L of distilled water)

<Production Medium (pH 7.0)>
Glucose 100 g, $(NH_4)_2SO_4$ 40 g, Soy Protein 2.5 g, Corn Steep Solids 5 g, Urea 3 g, $KH_2PO_4$ 1 g, $MgSO_4 \cdot 7H_2O$ 0.5 g, Biotin 100 µg, Thiamine-HCl 1000 µg, Calcium-Pantothenic Acid 2000 µg, Nicotinamide 3000 µg, $CaCO_3$ 30 g (based on 1 L of distilled water).

After completion of the culture, the L-lysine producing ability was measured by HPLC. The L-lysine concentration and concentration increase rate in the culture solution for each of the tested strains are shown in Table 4 below.

TABLE 4

| Name of Strains | L-Lysine Concentration (g/L) | L-Lysine Concentration Increase Rate (%) |
|---|---|---|
| KCCM11016P | 43 g/L | — |
| KCCM11016P::P(cj7)-gapN(S) | 50 g/L | 16% |
| KCCM11016P:::P(cj7)-gapN(L) | 52 g/L | 20% |
| KCCM11016P:::P(cj7)-gapN(C) | 47 g/L | 9% |

As shown in Table 4, it was confirmed that the concentration of L-lysine was increased by about 16% in the KCCM11016P::P(cj7)-gapN(S), by about 20% in the KCCM11016P:::P(cj7)-gapN(L), and by about 9% in the KCCM11016P:::P(cj7)-gapN(C), all of which were introduced with the gapN gene, as compared to the L-lysine-producing strain KCCM11016P.

The KCCM11016P:::P(cj7)-gapN(L) was named CA01-7528 and deposited at the Korean Culture Center of Microorganisms under Budapest Treaty on Sep. 2, 2019, with Accession No. KCCM12585P.

Example 2-2. Preparation of Strains Introduced with gapN(L), gapN(S), or gapN(C) in L-Lysine-Producing Strain KCCM11347P and Evaluation Thereof In order to confirm the lysine producing ability in other lysine-producing strains belonging to *Corynebacterium glutamicum*, strains introduced into KCCM11347P (Korean Patent No. 10-0073610), which is an L-lysine-producing strain, were prepared in the same manner as in Example 2-1 above using the plasmid prepared in Example 1-1-1, the plasmid prepared in Example 1-2, and the plasmid prepared in Example 1-3, and were named KCCM11347P:::P(cj7)-gapN(L), KCCM11347P::P(cj7)-gapN(S), and KCCM11347P:::P(cj7)-gapN(C), respectively.

The thus-prepared strains were cultured in the same manner as in Example 2-1 above, and the L-lysine producing ability was measured by HPLC after completion of the culture. The L-lysine concentration and concentration increase rate in the culture solution for each of the tested strains are shown in Table 5 below.

TABLE 5

| Name of Strains | L-Lysine Concentration (g/L) | L-Lysine Concentration Increase Rate (%) |
|---|---|---|
| KCCM11347P | 38 g/L | — |
| KCCM11347P::P(cj7)-gapN(S) | 43 g/L | 14% |
| KCCM11347P:::P(cj7)-gapN(L) | 45 g/L | 19% |
| KCCM11347P:::P(cj7)-gapN(C) | 40 g/L | 5% |

As shown in Table 5, it was confirmed that the concentration of L-lysine was increased by about 14% in the KCCM11347P::P(cj7)-gapN(S), by about 19% in the KCCM11347P:::P(cj7)-gapN(L), and by about 5% in the KCCM11347P:::P(cj7)-gapN(C), all of which were introduced with the gapN gene, as compared to the L-lysine-producing strain KCCM11347P.

Example 2-3. Preparation of Strains Introduced with gapN(L), gapN(S), or gapN(C) in L-Lysine-Producing Strain CJ3P and Evaluation Thereof In order to confirm the effect in other lysine-producing strains belonging to *Corynebacterium glutamicum*, strains introduced into *Corynebacterium glutamicum* CJ3P (Binder et al. *Genome Biology* 2012, 13:R40), which is an L-lysine-producing strain, were prepared in the same manner as in Example 2-1 above using the plasmid prepared in Example 1-1-1, the plasmid prepared in Example 1-2, and the plasmid prepared in Example 1-3, and were named CJ3P::P(cj7)-gapN(L), CJ3P::P(cj7)-gapN(S), and CJ3P::P(cj7)-gapN(C), respectively. The CJ3P strain is a *Corynebacterium glutamicum* strain having an L-lysine producing ability by introducing three kinds of mutations (pyc(Pro458Ser), hom (Val59Ala), lysC (Thr311Ile)) into a wild-type strain based on a known technique.

The thus-prepared strains were cultured in the same manner as in Example 2-1 above, and the L-lysine producing ability was measured by HPLC after completion of the culture. The L-lysine concentration and concentration increase rate in the culture solution for each of the tested strains are shown in Table 6 below.

TABLE 6

| Name of Strains | L-Lysine Concentration (g/L) | L-Lysine Concentration Increase Rate (%) |
|---|---|---|
| CJ3P | 8.3 g/L | — |
| CJ3P::P(cj7)-gapN(S) | 9.0 g/L | 8% |
| CJ3P::P(cj7)-gapN(L) | 9.4 g/L | 13% |
| CJ3P::P(cj7)-gapN(C) | 8.7 g/L | 4% |

As shown in Table 6, it was confirmed that the concentration of L-lysine was increased by about 8% in the CJ3P::P(cj7)-gapN(S), by about 13% in the CJ3P::P(cj7)-gapN(L), and by about 4% in the CJ3P::P(cj7)-gapN(C), all of which were introduced with the gapN gene, as compared to the L-lysine-producing strain CJ3P.

Example 2-4. Preparation of Strains Introduced with gapN(L), gapN(S), or gapN(C) in L-Lysine-Producing Strain KCCM10770P and Evaluation Thereof In order to confirm the effect in other lysine-producing strains belonging to *Corynebacterium glutamicum*, strains introduced into *Corynebacterium glutamicum* KCCM10770P (Korean Patent No. 10-0924065), which is an L-lysine-producing strain in which the lysine biosynthesis pathway has been enhanced, were prepared in the same manner as in Example 2-1 above using the plasmid prepared in Example 1-1-1, the plasmid prepared in Example 1-2, and the plasmid prepared in Example 1-3, and were named KCCM10770P::P(cj7)-gapN(L), KCCM10770P::P(cj7)-gapN(S), and KCCM10770P::P(cj7)-gapN(C), respectively. The KCCM10770P strain is an L-lysine producing strain having aspB (gene encoding aspartate aminotransferase), lysC (gene encoding aspartate kinase), asd (gene encoding aspartate-semialdehyde dehydrogenase), dapA (gene encoding dihydrodipicolinate synthase), dapB (gene encoding dihydrodipicolinate reductase), and lysA (gene encoding diaminopimelate decarboxylase), that is, a strain having 2 copies of each of 6 kinds of genes on the chromosome, among the genes constituting the lysine biosynthesis pathway.

The thus-prepared strains were cultured in the same manner as in Example 2-1 above, and the L-lysine producing ability was measured by HPLC after completion of the culture. The L-lysine concentration and concentration increase rate in the culture solution for each of the tested strains are shown in Table 7 below.

TABLE 7

| Name of Strains | L-Lysine Concentration (g/L) | L-Lysine Concentration Increase Rate (%) |
|---|---|---|
| KCCM10770P | 48 g/L | — |
| KCCM10770P::P(cj7)-gapN(S) | 56 g/L | 17% |
| KCCM10770P::P(cj7)-gapN(L) | 60 g/L | 25% |
| KCCM10770P::P(cj7)-gapN(C) | 53 g/L | 10% |

As shown in Table 7, it was confirmed that the concentration of L-lysine was increased by about 17% in the KCCM10770P::P(cj7)-gapN(S), by about 25% in the KCCM10770P::P(cj7)-gapN(L), and by about 10% in the KCCM10770P::P(cj7)-gapN(C), all of which were introduced with the gapN gene, as compared to the L-lysine-producing strain KCCM10770P.

From the results of Examples 2-1 to 2-4 above, it was found that the introduction of *L. delbrueckii* subsp. *bulgaricus*-derived gapN was effective for the L-lysine production in a variety of L-lysine-producing *Corynebacterium glutamicum* strains of different families. Further, it was confirmed that the strains introduced with *L. delbrueckii* subsp. *bulgaricus*-derived gapN showed an increased L-lysine producing ability as compared to the strains introduced with *S. mutans*-derived gapN of known Korean Patent No. 10-1182033 and strains introduced with *C. acetobutylicum*-derived gapN of known NCBI GenBank WP_010966919.1

Example 3-1. Preparation of Strains Introduced with gapN(L) or gapN(S) in L-Threonine-Producing Strain and Evaluation Thereof L-Threonine-producing strains were prepared by introducing a lysC(L377K) variant (Korean Patent No. 10-2011994) and a hom(R398Q) variant (Korean Patent No. 10-1947959) based on *Corynebacterium glutamicum* ATCC13032 (hereinafter referred to as WT) strain. Into these strains, the plasmid prepared in Example 1-1-2 and the plasmid prepared in Example 1-2 were introduced to prepare strains in the same manner as in Example 2-1 above, and the threonine producing ability was compared.

In order to prepare a vector for introducing lysC(L377K), PCR was performed using primers of SEQ ID NOS: 17 and 18 or primers of SEQ ID NOS: 19 and 20, based on the chromosome of the WT as a template. The PCR was performed by denaturation at 95° C. for 5 minutes, followed by 30 cycles of denaturation at 95° C. for 30 seconds, annealing at 55° C. for 30 seconds, and polymerization at 72° C. for 30 seconds, and then polymerization at 72° C. for 7 minutes. As a result, a 509 bp DNA fragment at the 5' upper region and a 520 bp DNA fragment at the 3' lower region were obtained around the mutation of the lysC gene.

Using the two amplified DNA fragments as templates, PCR was performed using the primers of SEQ ID NOS: 17 and 20 under PCR conditions of denaturation at 95° C. for 5 minutes, followed by 30 cycles of denaturation at 95° C. for 30 seconds, annealing at 55° C. for 30 seconds, and polymerization at 72° C. for 60 seconds, and then polymerization at 72° C. for 7 minutes. As a result, a 1011 bp DNA fragment containing the mutation of the lysC gene encoding the aspartokinase variant, in which the 377$^{th}$ leucine was substituted with lysine, was amplified.

The pDZ vector (Korean Patent No. 0924065), which cannot be replicated in *Corynebacterium glutamicum*, and the 1011 bp DNA fragment were treated with the restriction enzyme XbaI, ligated using a DNA ligation enzyme, and then cloned to obtain a plasmid, which was named pDZ-lysC (L377K).

The pDZ-lysC (L377K) vector obtained above was introduced into the WT strain by electroporation, and then the transformed strain was obtained in a selection medium containing 25 mg/L of kanamycin. Through a secondary crossover, WT::lysC (L377K), a strain in which a nucleotide mutation was introduced into the lysC gene by the DNA fragment inserted on the chromosome, was obtained.

TABLE 8

| SEQ ID NO: | Sequence (5'-3') |
|---|---|
| 17 | TCCTCTAGAGCTGCGCAGTGTTGAATACG |
| 18 | TGGAAATCTTTTCGATGTTCACGTTGACAT |
| 19 | ACATCGAAAAGATTTCCACCTCTGAGATTC |
| 20 | GACTCTAGAGTTCACCTCAGAGACGATTA |

Additionally, in order to prepare a vector for introducing hom(R398Q), PCR was performed using primers of SEQ ID NOS: 21 and 22, and primers of SEQ ID NOS: 23 and 24 based on the WT genomic DNA as a template. PCR was performed under PCR conditions of denaturation at 95° C. for 5 minutes, followed by 30 cycles of denaturation at 95° C. for 30 seconds, annealing at 55° C. for 30 seconds, and polymerization at 72° C. for 30 seconds, and then polymerization at 72° C. for 7 minutes. As a result, a 290 bp DNA fragment at the 5' upper region and a 170 bp DNA fragment at the 3' lower region were obtained around the mutation of the hom gene. Using the two amplified DNA fragments as templates, PCR was performed using the primers of SEQ ID NOS: 21 and 24 under conditions of denaturation at 95° C. for 5 minutes, followed by 30 cycles of denaturation at 95° C. for 30 seconds, annealing at 55° C. for 30 seconds, and polymerization at 72° C. for 30 seconds, and then polymerization at 72° C. for 7 minutes. As a result, a 440 bp DNA fragment containing the mutation of the hom gene was amplified.

TABLE 9

| SEQ ID NO: | Sequence (5'-3') |
|---|---|
| 21 | TCCTCTAGACTGGTCGCCTGATGTTCTAC |
| 22 | CTCTTCCTGTTGGATTGTAC |
| 23 | GTACAATCCAACAGGAAGAG |
| 24 | GACTCTAGATTAGTCCCTTTCGAGGCGGA |

The pDZ vector used above and the 440 bp DNA fragments were treated with the restriction enzyme XbaI, ligated using a DNA ligation enzyme, and then cloned to obtain a plasmid, which was named pDZ-hom(R398Q).

The pDZ-hom(R398Q) vector obtained above was introduced into the WT::lysC(L377K) strain by electroporation, and then the transformed strain was obtained in a selection medium containing 25 mg/L of kanamycin. Through secondary crossover, WT::lysC(L377K)-hom(R398Q), a strain in which a nucleotide mutation was introduced into the hom gene by the DNA fragment inserted on the chromosome, was obtained.

Strains were prepared in the same manner as in Example 2-1 above by introducing the plasmid prepared in Example 1-1-2 and the plasmid prepared in Example 1-2 into the WT::lysC(L377K)-hom (R398Q) strain, and were named WT::lysC(L377K)-hom(R398Q)::P(cj7)-gapN(L) and WT::lysC(L377K)-hom(R398Q)::P(cj7)-gapN(S), respectively.

The thus-prepared strains were cultured in the same manner as in Example 2-1 above, and after completion of the culture, the L-threonine producing ability was compared. The L-threonine concentration and concentrate increase rate in the culture solution for each of the tested strains are shown in Table 10 below.

TABLE 10

| Name of Strain | L-Threonine Concentration (g/L) | L-Threonine Concentration Increase Rate (%) |
|---|---|---|
| WT::lysC(L377K)-hom(R398Q) | 1.21 g/L | — |
| WT::lysC(L377K)-hom(R398Q)::P(cj7)-gapN(S) | 1.39 g/L | 15% |
| WT::lysC(L377K)-hom(R398Q)::P(cj7)-gapN(L) | 1.48 g/L | 22% |

As shown in Table 10, it was confirmed that the concentration of L-threonine was increased by about 15% in the WT::lysC(L377K)-hom(R398Q)::P(cj7)-gapN(S) and by about 22% in the WT::lysC(L377K)-hom(R398Q)::P(cj7)- gapN(L), both of which were introduced with the gapN gene, as compared to the WT::lysC(L377K)-hom(R398Q).

The WT::lysC(L377K)-hom(R398Q)::P(cj7)-gapN(L) was named CA09-0906 and deposited at the Korean Culture Center of Microorganisms under Budapest Treaty on Sep. 2, 2019, with Accession No. KCCM12586P.

Example 3-2. Preparation of Strains Introduced with gapN(L) or gapN(S) in L-Threonine-Producing Strain KCCM11222P and Evaluation Thereof Strains were prepared in the same manner as in Example 2-1 above by introducing the plasmid prepared in Example 1-1-2 and the plasmid prepared in Example 1-2 into *Corynebacterium glutamicum* KCCM11222P (WO 2013/081296), which is an L-threonine-producing strain, and were named KCCM11222P::P(cj7)-gapN(L) and KCCM11222P::P(cj7)-gapN(S), respectively.

The thus-prepared strains were cultured in the same manner as in Example 2-1 above, and after completion of the culture, the L-threonine producing ability was compared. The L-threonine concentration and concentrate increase rate in the culture solution for each of the tested strain are shown in Table 11 below.

TABLE 11

| Name of Strain | L-Threonine Concentration (g/L) | L-Threonine Concentration Increase Rate (%) |
| --- | --- | --- |
| KCCM11222P | 3.6 g/L | — |
| KCCM11222P::P(cj7)-gapN(S) | 4.1 g/L | 14% |
| KCCM11222P::P(cj7)-gapN(L) | 4.3 g/L | 20% |

As shown in Table 11, it was confirmed that the concentration of L-threonine was increased by about 14% in the KCCM11222P::P(cj7)-gapN(S) and by about 20% in the KCCM11222P::P(cj7)-gapN(L), both of which were introduced with the gapN gene, as compared to the L-threonine-producing strain KCCM11222P.

The results obtained from the above Examples suggest that the introduction of *L. delbrueckii* subsp. *bulgaricus*-derived gapN is effective for the L-threonine production in the L-threonine-producing strains belonging to the genus *Corynebacterium*.

Example 4-1. Preparation of Strains Introduced with gapN(L) or gapN(S) in L-Isoleucine-Producing Strain and Evaluation Thereof In order to confirm the effect of introducing *L. delbrueckii* subsp. *bulgaricus*- or *S. mutans*-derived gapN on the L-isoleucine producing ability based on *Corynebacterium glutamicum* ATCC13032 (hereinafter referred to as WT) strain, a strain having an enhanced L-isoleucine producing ability was prepared by introducing a mutation of ilvA (ilvA (V323A); S. Morbach et al., Appl. Enviro. Microbiol., 62(12): 4345-4351, 1996), which is the known gene encoding L-threonine dehydratase.

A primer pair (SEQ ID NOS: 25 and 26) for the amplification of the 5' upper region and a primer pair (SEQ ID NOS: 27 and 28) for the amplification of the 3' lower region were designed around the mutation site in order to prepare a vector for introducing a mutation based on the ilvA gene. The primers of SEQ ID NOS: 25 and 28 were inserted with a BamHI restriction enzyme site (indicated by underline) at each end, and the primers of SEQ ID NOS: 26 and 27 were designed to crossover with each other so as to locate the nucleotide substitution mutations (indicated by underline) at the designed sites.

TABLE 12

| SEQ ID NO: | Sequence (5'-3') |
| --- | --- |
| 25 | ACGGATCCCAGACTCCAAAGCAAAAGCG |
| 26 | ACACCACGGCAGAACCAGGTGCAAAGGACA |
| 27 | CTGGTTCTGCCGTGGTGTGCATCATCTCTG |
| 28 | ACGGATCCAACCAAACTTGCTCACACTC |

PCR was performed using the primers of SEQ ID NO: 25, SEQ ID NO: 26, SEQ ID NO: 27, and SEQ ID NO: 28 based on the WT chromosome as a template. PCR was performed under PCR conditions of denaturation at 95° C. for 5 minutes, followed by 30 cycles of denaturation at 95° C. for 30 seconds, annealing at 55° C. for 30 seconds, and polymerization at 72° C. for 30 seconds, and then polymerization at 72° C. for 7 minutes. As a result, a 627 bp DNA fragment at the 5' upper region and a 608 bp DNA fragment at the 3' lower region were obtained around the mutation of the ilvA gene.

Using the two amplified DNA fragments as templates, PCR was performed using the primers of SEQ ID NOS: 25 and 28 under conditions of denaturation at 95° C. for 5 minutes, followed by 30 cycles of denaturation at 95° C. for 30 seconds, annealing at 55° C. for 30 seconds, and polymerization at 72° C. for 60 seconds, and then polymerization at 72° C. for 7 minutes. As a result, a 1217 bp DNA fragment containing the mutation of the ilvA gene encoding the ilvA variant in which valine at the $323^{th}$ position is substituted with alanine was amplified.

The pECCG117 (Korean Patent No. 10-0057684) and the 1011 bp DNA fragments were treated with the restriction enzyme BamHI, ligated using a DNA ligation enzyme, and then cloned to obtain a plasmid, which was named pECCG117-ilvA(V323A).

Strains in which the ilvA(V323A) mutation was introduced were prepared by introducing the pECCG117-ilvA (V323A) vector into the WT::lysC(L377K)-hom(R398Q):: P(cj7)-gapN(L) and WT::lysC(L377K)-hom(R398Q)::P (cj7)-gapN(S) of Example 3-1. Additionally, a strain in which only the ilvA (V323A) mutation was introduced into WT::lysC(L377K)-hom(R398Q) was prepared as a control.

The thus-prepared strains were cultured in the same manner as in Example 2-1 above to compare the L-isoleucine producing ability. The L-isoleucine concentration and concentration increase rate in the culture solution for each of the tested strains are shown in Table 13 below.

TABLE 13

| Name of Strains | L-Isoleucine Concentration (g/L) | L-Isoleucine Concentration Increase Rate (%) |
| --- | --- | --- |
| WT::lysC(L377K)-hom(R398Q)/ pECCG117-ilvA(V323A) | 4.3 g/L | — |
| WT::lysC(L377K)-hom(R398Q)::P(cj7)-gapN(S)/ pECCG117-ilvA(V323A) | 5.1 g/L | 18% |

TABLE 13-continued

| Name of Strains | L-Isoleucine Concentration (g/L) | L-Isoleucine Concentration Increase Rate (%) |
|---|---|---|
| WT::lysC(L377K)-hom(R398Q)::P(cj7)-gapN(L)/pECCG117-ilvA(V323A) | 5.6 g/L | 30% |

As shown in Table 13, it was confirmed that the concentration of L-isoleucine was increased by about 18.6% in the WT::lysC(L377K)-hom(R398Q)::P(cj7)-gapN(S)/pECCG117-ilvA(V323A) and by about 30% in the WT::lysC(L377K)-hom(R398Q)::P(cj7)-gapN(L)/pECCG117-ilvA(V323A), both of which were introduced with the gapN gene, as compared to the WT::lysC(L377K)-hom(R398Q)/pECCG117-ilvA(V323A).

The WT::lysC(L377K)-hom(R398Q)::P(cj7)-gapN(L)/pECCG117-ilvA(V323A) was named CA10-3108 and deposited at the Korean Culture Center of Microorganisms under Budapest Treaty on Sep. 2, 2019, with Accession No. KCCM12582P.

Example 4-2. Preparation of Strains Introduced with gapN(L) or gapN(S) in L-Isoleucine-Producing Strain KCCM11248P and Evaluation Thereof Strains were prepared in the same manner as in Example 2-1 above by introducing the plasmid prepared in Example 1-1-2 and Example 1-2 into *Corynebacterium glutamicum* KCCM11248P (Korean Patent No. 10-1335789), which is an L-isoleucine-producing strain, and were named KCCM11248P::P(cj7)-gapN(L) and KCCM11248P::P(cj7)-gapN(S), respectively.

The thus-prepared strains were cultured in the same manner as in Example 2-1 above, and the L-isoleucine producing ability was compared. After completion of the culture, the L-isoleucine producing ability was measured by HPLC, and the L-isoleucine concentration and concentrate increase rate in the culture solution for each of the tested strains are shown in Table 14 below.

TABLE 14

| Name of Strains | L-Isoleucine Concentration (g/L) | L-Isoleucine Concentration Increase Rate (%) |
|---|---|---|
| KCCM11248P | 1.3 g/L | — |
| KCCM11248P::P(cj7)-gapN(S) | 1.8 g/L | 38% |
| KCCM11248P::P(cj7)-gapN(L) | 2.1 g/L | 61.5% |

As shown in Table 14, it was confirmed that the concentration of L-isoleucine was increased by about 38% in the KCCM11248P::P(cj7)-gapN(S) and by about 61.5% in the KCCM11248P::P(cj7)-gapN(L), both of which were introduced with the gapN gene, as compared to the L-isoleucine-producing strain KCCM11248P.

The results obtained from the Examples suggest that the introduction of *L. delbrueckii* subsp. *bulgaricus*-derived gapN is effective for the L-isoleucine production in the L-isoleucine-producing strains belonging to the genus *Corynebacterium*.

Example 5-1. Preparation of Strains Introduced with gapN(L) or gapN(S) in L-Leucine-Producing Strain and Evaluation Thereof In order to confirm the effect of introducing *L. delbrueckii* subsp. *bulgaricus*- or *S. mutans*-derived gapN on the L-leucine producing ability based on *Corynebacterium glutamicum* ATCC13032 strain, a strain having an enhanced L-leucine producing ability was prepared by introducing a mutation of leuA synthase (leuA (R558H, G561 D); Korean Application Publication No. 2018-0077008), which is the known gene encoding 2-isopropylmalate synthase.

Specifically, the recombinant plasmid pDZ-leuA(R558H, G561 D) prepared in the patent above was introduced into the WT strain by electroporation, and then selected in a medium containing 25 mg/L of kanamycin. Through secondary crossover, WT::leuA(R558H, G561 D), a strain in which a nucleotide mutation was introduced into the leuA gene by the DNA fragment inserted on the chromosome, was obtained, which was named CJL8001.

Strains were prepared in the same manner as in Example 2-1 above by introducing the plasmid prepared in Example 1-1-1 and the plasmid prepared in Example 1-2 into the *Corynebacterium glutamicum* CJL8001 having the L-leucine producing ability, and were named CJL8001::P(cj7)-gapN(S) and CJL8001::P(cj7)-gapN(L), respectively.

The thus-prepared strains were cultured in the following manner to compare the L-leucine producing ability. Each strain was subcultured in a nutrient medium, and then seeded into a 250 mL corner-baffle flask containing 25 mL of a production medium and cultured at 30° C. for 72 hours at 200 rpm with shaking. Then, the concentration of L-leucine was analyzed by HPLC, and the analyzed L-leucine concentration and concentration increase rate are shown in Table 15.

<Nutrient Medium (pH 7.2)>

Glucose 10 g, Meat Extract 5 g, Polypeptone 10 g, Sodium Chloride 2.5 g, Yeast Extract 5 g, Agar 20 g, Urea 2 g (based on 1 L of distilled water)

<Production Medium (pH 7.0)>

Glucose 50 g, Ammonium Sulfate 20 g, Corn Steep Solids 20 g, $K_2HPO_4$ 1 g, $MgSO_4 \cdot 7H_2O$ 0.5 g, Biotin 100 μg, Thiamine-HCl 1 mg, Calcium Carbonate 15 g (based on 1 L of distilled water)

TABLE 15

| Name of Strains | L-Leucine Concentration (g/L) | L-Leucine Concentration Increase Rate (%) |
|---|---|---|
| CJL8001 | 3.4 g/L | — |
| CJL8001::P(cj7)-gapN(S) | 3.9 g/L | 15% |
| CJL8001::P(cj7)-gapN(L) | 4.1 g/L | 21% |

As shown in Table 15, it was confirmed that the concentration of L-isoleucine was increased by about 15% in the CJL8001::P(cj7)-gapN(S) and by about 21% in the CJL8001::P(cj7)-gapN(L), both of which were introduced with the gapN gene, as compared to the L-leucine-producing strain CJL8001.

The CJL8001::P(cj7)-gapN(L) was named CA13-8102 and deposited at the Korean Culture Center of Microorganisms under Budapest Treaty on Sep. 2, 2019, with Accession No. KCCM12583P.

Example 5-2: Preparation of Strains Introduced with gapN(L) or gapN(S) in L-Leucine-Producing Strains KCCM11661P and KCCM11662P and Evaluation Thereof Strains were prepared in the same manner as in Example 2-1 above by introducing the plasmid prepared in Example 1-1-1 and the plasmid prepared in Example 1-2 into *Coryne-* bacterium glutamicum KCCM11661P (Korean Patent No. 10-1851898) and KCCM11662P (Korean Patent No. 10-1796830), which are L-leucine-producing strains, and were named KCCM11661P::P(cj7)-gapN(L), KCCM11661P::P(cj7)-gapN(S), KCCM11662P::P(cj7)-gapN(L), and KCCM11662P::P(cj7)-gapN(S).

The thus-prepared strains were cultured in the same manner as in Example 5-1, and after completion of the culture, the L-leucine producing ability was compared. The concentration of L-leucine produced in each strain and concentration increase rate are shown in Table 16 below.

TABLE 16

| Name of Strains | L-Leucine Concentration (g/L) | L-Leucine Concentration Increase Rate (%) |
| --- | --- | --- |
| KCCM11661P | 2.7 g/L | — |
| KCCM11661P::P(cj7)-gapN(S) | 2.8 g/L | 4% |
| KCCM11661P::P(cj7)-gapN(L) | 3.0 g/L | 11% |
| KCCM11662P | 3.0 g/L | — |
| KCCM11662P::P(cj7)-gapN(S) | 3.1 g/L | 3% |
| KCCM11662P::P(cj7)-gapN(L) | 3.3 g/L | 11% |

As shown in Table 16, it was confirmed that the concentration of L-leucine was increased by about 4% in the KCCM11661P::P(cj7)-gapN(S) and KCCM11662P::P(cj7)-gapN(S), and by about 11% in the KCCM11661P::P(cj7)-gapN(L) and KCCM11662P::P(cj7)-gapN(L), all of which were introduced with the gapN gene, as compared to the L-leucine-producing strains KCCM11661P and KCCM11662P.

The results obtained from the Examples suggest that the introduction of *L. delbrueckii* subsp. *bulgaricus*-derived gapN is effective for the L-leucine production in the L-leucine-producing strains belonging to the genus *Corynebacterium*.

Example 6-1. Preparation of Strains Introduced with gapN(L) or gapN(S) in L-Valine-Producing Strain and Evaluation Thereof In order to confirm the effect of introducing *L. delbrueckii* subsp. *bulgaricus*- or *S. mutans*-derived gapN on the L-valine producing ability, a variant was prepared by introducing one type of mutation (ilvN(A42V); Biotechnology and Bioprocess Engineering, June 2014, Volume 19, Issue 3, pp. 456-467) into the wild-type *Corynebacterium glutamicum* ATCC13869 strain to have an L-valine producing ability, and the resulting recombinant strain was named *Corynebacterium glutamicum* CJ8V.

Specifically, PCR was performed based on the genomic DNA of the wild-type *Corynebacterium glutamicum* ATCC13869 strain as a template. In order to prepare a vector for introducing A42V mutation into the ilvN gene, gene fragments (A and B) were obtained using a primer pair of SEQ ID NOS: 29 and 30 and a primer pair of SEQ ID NOS: 31 and 32. PCR was performed under PCR conditions of denaturation at 94° C. for 5 minutes, followed by 30 cycles of denaturation at 94° C. for 30 seconds, annealing at 55° C. for 30 seconds, and polymerization at 72° C. for 60 seconds, and then polymerization at 72° C. for 7 minutes.

As a result, 537 bp polynucleotides were obtained for both fragments A and B. Overlapping PCR was performed using the primers of SEQ ID NO: 29 and SEQ ID NO: 32 based on the two fragments as templates to obtain a 1044 bp DNA fragment.

The thus-obtained 1044 bp DNA fragment and the pDZ vector used above were treated with the restriction enzyme XbaI, ligated using a ligation enzyme, and then cloned to obtain a plasmid, which was named pDZ-ilvN(A42V).

TABLE 17

| SEQ ID NO: | Sequence (5'-3') |
| --- | --- |
| 29 | AATTTCTAGAGGCAGACCCTATTCTATGAAGG |
| 30 | AGTGTTTCGGTCTTTACAGACACGAGGGAC |
| 31 | GTCCCTCGTGTCTGTAAAGACCGAAACACT |
| 32 | AATTTCTAGACGTGGGAGTGTCACTCGCTTGG |

The thus-prepared recombinant plasmid pDZ-ilvN (A42V) was introduced into the wild-type *Corynebacterium glutamicum* ATCC13869 strain by electroporation, and then the transformed strain was obtained in a selection medium containing 25 mg/L of kanamycin. The gene fragments were amplified by PCR using the primers of SEQ ID NO: 29 and SEQ ID NO: 32 based on the transformed *Corynebacterium glutamicum* strain, in which the second recombination was completed, and then the strain introduced with the mutation was confirmed by gene sequencing. The resulting recombinant strain was named *Corynebacterium glutamicum* CJ8V.

Lastly, strains were prepared in the same manner as in Example 2-1 above by introducing the plasmid prepared in Example 1-1-3 and the plasmid prepared in Example 1-2 into the *Corynebacterium glutamicum* CJ8V having an L-valine producing ability, and were named CJ8V::P(cj7)-gapN(L) and CJ8V::Pcj7-gapN(S), respectively. The thus-prepared strains were cultured in the following manner to compare the L-valine producing ability.

Each strain was subcultured in a nutrient medium, and then seeded into a 250 mL corner-baffle flask containing 25 mL of a production medium and cultured at 30° C. for 72 hours at 200 rpm with shaking. Then, the concentration of L-valine was analyzed by HPLC, and the analyzed L-valine concentration and concentration increase rate are shown in Table 18.

<Nutrient Medium (pH 7.2)>
Glucose 10 g, Meat Extract 5 g, Polypeptone 10 g, Sodium Chloride 2.5 g, Yeast Extract 5 g, Agar 20 g, Urea 2 g (based on 1 L of distilled water)

<Production Medium (pH 7.0)>
Glucose 100 g, Ammonium Sulfate 40 g, Soy Protein 2.5 g, Corn Steep Solids 5 g, Urea 3 g, $K_2HPO_4$ 1 g, $MgSO_4 \cdot 7H_2O$ 0.5 g, Biotin 100 µg, Thiamine-HCl 1 mg, Calcium-Pantothenic Acid 2 mg, Nicotinamide 3 mg, Calcium Carbonate 30 g (based on 1 L of distilled water)

TABLE 18

| Name of Strains | L-Valine Concentration (g/L) | L-Valine Concentration Increase Rate (%) |
| --- | --- | --- |
| CJ8V | 3.4 g/L | — |
| CJ8V-Pcj7/gapN(S) | 3.8 g/L | 12% |
| CJ8V-Pcj7/gapN(L) | 4.0 g/L | 18% |

As shown in Table 18, it was confirmed that the L-valine producing ability of CJ8V-Pcj7/gapN(L) and CJ8V-Pcj7/gapN(S) strains was increased by 18% and 12%, respectively, as compared to the control.

As a result, it was confirmed that the introduction of the *L. delbrueckii* subsp. *bulgaricus*- or *S. mutans*-derived gapN gene can improve the L-valine producing ability in the L-valine-producing strains belonging to the genus *Corynebacterium*.

The CJ8V-Pcj7/gapN(L) was named CA08-2038 and deposited at the Korean Culture Center of Microorganisms under Budapest Treaty on Sep. 2, 2019, with Accession No. KCCM12581P.

Example 6-2. Preparation of Strains Introduced with gapN(L) or gapN(S) in L-Valine-Producing Strain KCCM11201P and Evaluation Thereof Strains were prepared in the same manner as in Example 2-1 above by introducing the plasmid prepared in Example 1-1-3 and the plasmid prepared in Example 1-2 into the *Corynebacterium glutamicum* KCCM11201P (Korean Patent No. 10-1117022), which is an L-valine-producing strain, and were named KCCM11201P::P(cj7)-gapN(L) and KCCM11201P::P(cj7)-gapN(S), respectively.

In order to compare the L-valine producing ability, the thus-prepared strains were cultured in the same manner as in Example 6-1. Then, the concentration of L-valine was analyzed, and the analyzed L-valine concentration and concentration increase rate are shown in Table 19.

TABLE 19

| Name of Strains | L-Valine Concentration (g/L) | L-Valine Concentration Increase Rate (%) |
| --- | --- | --- |
| KCCM11201P | 2.8 g/L | — |
| KCCM11201P::P(cj7)-gapN(S) | 3.3 g/L | 17% |
| KCCM11201P::P(cj7)-gapN(L) | 3.7 g/L | 32% |

As shown in Table 19, it was confirmed that the L-valine producing ability of KCCM11201P::P(cj7)-gapN(L) and KCCM11201P::P(cj7)-gapN(S) strains was increased by 32.1% and 17.9%, respectively, as compared to the control.

As a result, it was confirmed that the introduction of *L. delbrueckii* subsp. *bulgaricus*- or *S. mutans*-derived gapN gene can improve the L-valine producing ability in the L-valine-producing strains belonging to the genus *Corynebacterium*.

Example 7-1. Preparation of Strains Introduced with gapN(L) or gapN(S) in L-Arginine-Producing Strain and Evaluation Thereof In order to confirm the effect of introducing *L. delbrueckii* subsp. *bulgaricus*- or *S. mutans*-derived gapN on the L-arginine producing ability, strains were prepared in the same manner as in Example 2-1 above by introducing the plasmid prepared in Example 1-1-3 and the plasmid prepared in Example 1-2 based into the wild-type *Corynebacterium glutamicum* ATCC21831 strain, and were named ATCC21831::P(cj7)gapN(L) and ATCC21831::P(cj7)-gapN(S), respectively.

The thus-prepared strains were cultured in the following manner to compare the L-arginine producing ability. Each strain was subcultured in a nutrient medium, and then seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of a production medium, and cultured at 30° C. for 72 hours at 200 rpm with shaking. Compositions of the nutrient medium, seed medium and production medium are shown below. After completion of the culture, the production amount of L-arginine was measured by HPLC, and the analyzed L-arginine concentration and concentration increase rate are shown in Table 20 below.

<Nutrient Medium (pH 7.2)>

Glucose 10 g, Meat Extract 5 g, Polypeptone 10 g, Sodium Chloride 2.5 g, Yeast Extract 5 g, Agar 20 g, Urea 2 g (based on 1 L of distilled water)

<Seed Medium (pH 7.0)>

Sucrose 20 g, Peptone 10 g, Yeast Extract 5 g, Urea 1.5 g, $KH_2PO_4$ 4 g, $K_2HPO_4$ 8 g, $MgSO_4 \cdot 7H_2O$ 0.5 g, Biotin 100 μg, Thiamine-HCl 1 mg, Calcium-Pantothenic Acid 2 mg, Nicotinamide 2 mg (based on 1 L of distilled water)

<Production Medium (pH 7.0)>

Sucrose 6%, Ammonium Sulfate 3%, $KH_2PO_4$ 0.1%, $MgSO_4 \cdot 7H_2O$ 0.2%, CSL (Corn Steep Solids) 1.5%, NaCl 1%, Yeast Extract 0.5%, Biotin 100 mg/L (based on 1 L of distilled water)

TABLE 20

| Name of Strains | L-Arginine Concentration (g/L) | L- Arginine Concentration Increase Rate (%) |
| --- | --- | --- |
| ATCC21831 | 4.1 g/L | — |
| ATCC21831::P(cj7)-gapN(S) | 4.6 g/L | 12% |
| ATCC21831::P(cj7)-gapN(L) | 4.9 g/L | 19% |

As shown in Table 20, it was confirmed that the L-arginine producing ability of ATCC21831::P(cj7)-gapN(L) and ATCC21831::P(cj7)-gapN(S) strains was increased by 19.5% and 12.1%, respectively, as compared to the control.

The ATCC21831::P(cj7)-gapN(L) was named CA06-2951 and deposited at the Korean Culture Center of Microorganisms under Budapest Treaty on Sep. 2, 2019, with Accession No. KCCM12580P.

As a result, it was confirmed that the introduction of *L. delbrueckii* subsp. *bulgaricus*- or *S. mutans*-derived gapN gene can improve the L-arginine producing ability in the L-arginine-producing strains belonging to the genus *Corynebacterium*.

Example 7-2. Preparation of Strains Introduced with gapN(L) or gapN(S) in L-Arginine-Producing Strain KCCM10741P and Evaluation Thereof Strains were prepared in the same manner as in Example 2-1 above by introducing the plasmid prepared in Example 1-1-3 and the plasmid prepared in Example 1-2 into the *Corynebacterium glutamicum* KCCM10741P (Korean Patent No. 10-0791659), which is an L-arginine-producing strain, and were named KCCM10741P::P(cj7)-gapN(L) and KCCM10741P::P(cj7)-gapN(S), respectively.

In order to compare the L-arginine producing ability, the thus-prepared strains were cultured in the same manner as in Example 7-1. Then, the concentration of L-arginine was analyzed, and the analyzed L-arginine concentration and concentration increase rate are shown in Table 21.

TABLE 21

| Name of Strains | L-Arginine Concentration (g/L) | L-Arginine Concentration Increase Rate (%) |
|---|---|---|
| KCCM10741P | 3.1 g/L | — |
| KCCM10741P::P(cj7)-gapN(S) | 3.4 g/L | 9% |
| KCCM10741P::P(cj7)-gapN(L) | 3.8 g/L | 22% |

As shown in Table 21, it was confirmed that the L-arginine producing ability of KCCM10741P::P(cj7)-gapN(L) and KCCM10741P::P(cj7)-gapN(S) strains was increased by 22.6% and 9.7%, respectively, as compared to the control.

As a result, it was confirmed that the introduction of *L. delbrueckii* subsp. *bulgaricus*- or *S. mutans*-derived gapN gene can improve the L-arginine producing ability in the L-arginine-producing strains belonging to the genus *Corynebacterium*.

Example 8-1. Preparation of Strains Introduced with gapN(L) or gapN(S) in O-Acetyl Homoserine-Producing Strain and Evaluation Thereof Strains were prepared in the same manner as in Example 2-1 above by introducing the plasmid prepared in Example 1-1-1 and the plasmid prepared in Example 1-2 to the wild-type *Corynebacterium glutamicum* ATCC13032 strain, and were named ATCC13032::P(cj7)-gapN(L) and ATCC13032::P(cj7)-gapN(S), respectively. The thus-prepared strains were cultured in the following manner to compare the O-acetyl homoserine producing ability.

Each strain was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 24 mL of a production medium, and cultured at 30° C. for 48 hours at 200 rpm with shaking. Compositions of the seed medium and production medium are shown below.

<Seed Medium (pH 7.0)>

Glucose 20 g, Peptone 10 g, Yeast Extract 5 g, Urea 1.5 g, $KH_2PO_4$ 4 g, $K_2HPO_4$ 8 g, $MgSO_4 \cdot 7H_2O$ 0.5 g, Biotin 100 µg, Thiamine-HCl 1000 µg, Calcium-Pantothenic Acid 2000 µg, Nicotinamide 2000 µg (based on 1 L of distilled water)

<Production Medium (pH 7.0)>

Glucose 50 g, $(NH_4)_2SO_4$ 12.5 g, Soy Protein 2.5 g, Corn Steep Solids 5 g, Urea 3 g, $KH_2PO_4$ 1 g, $MgSO_4 \cdot 7H_2O$ 0.5 g, Biotin 100 µg, Thiamine-HCl 1000 µg, Calcium-Pantothenic Acid 2000 µg, Nicotinamide 3000 µg, $CaCO_3$ 30 g (based on 1 L of distilled water)

After completion of the culture, the O-acetyl homoserine producing ability was measured by HPLC. The O-acetyl homoserine concentration and concentration increase rate in the culture solution for each of the tested strains are shown in Table 22 below.

TABLE 22

| Name of Strains | O-Acetyl Homoserine Concentration (g/L) | O-Acetyl Homoserine Concentration Increase Rate (%) |
|---|---|---|
| ATCC13032 | 0.3 g/L | — |
| ATCC13032::P(cj7)-gapN(S) | 0.4 g/L | 33% |
| ATCC13032::P(cj7)-gapN(L) | 0.5 g/L | 67% |

As shown in Table 22, it was confirmed that the concentration of O-acetyl homoserine was increased by about 33% in the ATCC13032::P(cj7)-gapN(S) and by about 67% in the ATCC13032::P(cj7)-gapN(L), both of which were introduced with the gapN gene, as compared to the wild-type ATCC13032 strain.

The ATCC13032::P(cj7)-gapN(L) was named CM04-0531 and deposited at the Korean Culture Center of Microorganisms under Budapest Treaty on Sep. 2, 2019, with Accession No. KCCM12584P.

Example 8-2. Preparation of Strains Introduced with *L. delbrueckii* Subsp. *Bulgaricus*-Derived gapN(L) or *S. mutans*-Derived gapN(S) in O-Acetyl Homoserine-Producing *Corynebacterium glutamicum* Strain and Evaluation Thereof In order to confirm the effect of introducing *L. delbrueckii* subsp. *bulgaricus*- or *S. mutans*-derived gapN on the O-acetyl homoserine producing ability, the autogenous homoserine O-acetyltransferase of *Corynebacterium glutamicum* was enhanced.

In order to amplify the gene encoding O-acetyl homoserine transferase (MetX), primers of SEQ ID NOS: 33 and 34 were designed for amplification from a promoter region (located about 300 bp upstream from a start codon) to a terminator region (located about 100 bp downstream from a stop codon) based on a reported sequence derived from wild-type (WT). The BamHI restriction enzyme site was inserted into both ends of each of primers of SEQ ID NOS: 33 and 34. PCR was performed under PCR conditions of denaturation at 95° C. for 5 minutes, followed by 30 cycles of denaturation at 95° C. for 30 seconds, annealing at 55° C. for 30 seconds, and polymerization at 72° C. for 90 seconds, and then polymerization at 72° C. for 7 minutes. As a result, a 1546 bp DNA fragment was obtained in the coding region of the metX gene. The pECCG117 vector (Korean Patent No. 10-0057684) and the metX DNA fragment were treated with the restriction enzyme BamHI, ligated using a DNA ligase, and cloned to obtain a plasmid which was named pECCG117-metX WT.

TABLE 23

| SEQ ID NO: | Sequence (5'-3') |
|---|---|
| 33 | GGATCCCCTCGTTGTTCACCCAGCAACC |
| 34 | GGATCCCAAAGTCACAACTACTTATGTTAG |

Strains, in which the autogenous metX of *Corynebacterium glutamicum* was overexpressed, were prepared by introducing the pECCG117-metX WT into WT::lysC(L377K)-hom(R398Q)::P(cj7)-gapN(L) and WT::lysC(L377K)-hom(R398Q)::P(cj7)-gapN(S) strains of Example 3-1 above. Further, the same vector was introduced into the WT::lysC(L377K)-hom(R398Q) as a control.

The thus-prepared strains were cultured in the same manner as the flask culture method of Example 8-1 to analyze the O-acetyl homoserine concentration and concentration increase rate in the culture solution. The results are shown in Table 24.

TABLE 24

| Name of Strains | O-Acetyl Homoserine Concentration (g/L) | O-Acetyl Homoserine Concentration Increase Rate (%) |
|---|---|---|
| WT::lysC(L377K)-hom(R398Q)/pECCG117-metX WT | 2.0 g/L | — |
| WT::lysC(L377K)-hom(R398Q)::P(cj7)-gapN(S)/pECCG117-metX WT | 2.7 g/L | 35% |
| WT::lysC(L377K)-hom(R398Q)::P(cj7)-gapN(L)/pECCG117-metX WT | 3.1 g/L | 55% |

As shown in Table 24, it was confirmed that the concentration of O-acetyl homoserine was increased by about 35% in the WT::lysC(L377K)-hom(R398Q)::P(cj7)-gapN(S)/pECCG117-metX WT and by about 55% in the WT::lysC(L377K)-hom(R398Q)::P(cj7)-gapN(L)/pECCG117-metX WT, both of which were introduced with the gapN gene, as compared to the WT::lysC(L377K)-hom(R398Q)/pECCG117-metX WT.

The results obtained from the Examples suggest that the introduction of *L. delbrueckii* subsp. *bulgaricus*-derived gapN is effective for the O-acetyl homoserine production in the wild-type strains belonging to the genus *Corynebacterium*.

Example 9-1. Preparation of Strains Introduced with gapN(L) or gapN(S) in Glutamic Acid-Producing Strain and Evaluation Thereof In order to confirm the effect of introducing *L. delbrueckii* subsp. *bulgaricus*- or *S. mutans*-derived gapN on the glutamic acid producing ability, strains were prepared in the same manner as in Example 2-1 above by introducing the plasmid prepared in Example 1-1-4 and the plasmid prepared in Example 1-2 based on the wild-type *Corynebacterium glutamicum* ATCC13869 strain, and were named ATCC13869::P(cj7)-gapN(L) and ATCC13869::P(cj7)-gapN(S), respectively.

Each strain was seeded into a 250 mL corner-baffle flask containing 25 mL of a seed medium and cultured at 30° C. for 20 hours at 200 rpm with shaking. Then, 1 mL of the seed culture solution was seeded into a 250 mL corner-baffle flask containing 25 mL of a production medium, and cultured at 30° C. for 40 hours at 200 rpm with shaking. The culture was carried out under biotin-restricted conditions. After completion of the culture, the L-glutamic acid concentration and concentration increase rate were measured by HPLC, and the measurement results are shown in Table 25 below.

<Seed Medium (pH 7.2)>

Glucose 1%, Meat Extract 0.5%, Polypeptone 1%, Sodium Chloride 0.25%, Yeast Extract 0.5%, Agar 2%, Urea 0.2%

<Production Medium>

Raw Sugar 6%, Calcium Carbonate 5%, Ammonium sulfate 2.25%, $KH_2PO_4$ 0.1%, Magnesium Sulfate 0.04%, Iron sulfate 10 mg/L, Thiamine-HCl 0.2 mg/L

TABLE 25

| Name of Strains | L-Glutamic Acid Concentration (g/L) | L-Glutamic Acid Concentration Increase Rate (%) |
|---|---|---|
| ATCC13869 | 0.5 g/L | — |
| ATCC13869::P(cj7)-gapN(S) | 0.8 g/L | 60% |
| ATCC13869::P(cj7)-gapN(L) | 0.9 g/L | 80% |

As shown in Table 25, it was confirmed that the concentration of glutamic acid was increased by about 60% in the ATCC13869::P(cj7)-gapN(S) and by about 80% in the ATCC13869::P(cj7)-gapN(L), both of which were introduced with the gapN gene, as compared to the wild-type ATCC13869 strain.

The ATCC13869::P(cj7)-gapN(L) was named CA02-1360 and deposited at the Korean Culture Center of Microorganisms under Budapest Treaty on Sep. 2, 2019, with Accession No. KCCM12587P.

Example 9-2. Preparation of Strains Introduced with gapN(L) or gapN(S) in Glutamic Acid-Producing Strain KFCC11074 and Evaluation Thereof Strains were prepared in the same manner as in Example 2-1 above by introducing the plasmid prepared in Example 1-1-4 and the plasmid prepared in Example 1-2 into the *Corynebacterium glutamicum* KFCC11074 strain(Korean Patent No. 10-0292299), which is an L-glutamic acid-producing strain, and were named KFCC11074::P(cj7)-gapN(L) and KFCC11074::P(cj7)-gapN(S), respectively.

The thus-prepared strains were cultured in the same manner as in Example 10-1 to compare the L-glutamic acid producing ability. After completion of the culture, the L-glutamic acid concentration was analyzed, and the analyzed L-glutamic acid concentration and concentration increase rate are shown in Table 26.

TABLE 26

| Name of Strains | L-Glutamic Acid Concentration (g/L) | L-Glutamic Acid Concentration Increase Rate (%) |
|---|---|---|
| KFCC11074 | 11.8 g/L | — |
| KFCC11074::P(cj7)-gapN(S) | 14.5 g/L | 22% |
| KFCC11074::P(cj7)-gapN(L) | 16.2 g/L | 37% |

As shown in Table 26, it was confirmed that the concentration of glutamic acid was increased by about 22.9% in the KFCC11074::P(cj7)-gapN(S) and by about 37.3% in the KFCC11074::P(cj7)-gapN(L), both of which were introduced with the gapN gene, as compared to KFCC11074.

As a result, it was confirmed that the introduction of the *L. delbrueckii* subsp. *bulgaricus*- or *S. mutans*-derived gapN gene can improve the L-glutamic acid producing ability in the L-glutamic acid-producing strains belonging to the genus *Corynebacterium*.

In conclusion, the results obtained from Examples 1 to 9 suggest that the introduction of the *L. delbrueckii* subsp. *bulgaricus*- or *S. mutans*-derived gapN gene can improve the L-amino acid producing ability in the L-glutamic acid-producing strains belonging to the genus *Corynebacterium*, and in particular, it was confirmed that the introduction of the *L. delbrueckii* subsp. *bulgaricus*-derived gapN gene showed superior L-amino acid producing ability compared to the introduction of the *S. mutans*-derived gapN gene.

Those of ordinary skill in the art to which the present disclosure belongs will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A method for producing an L-amino acid, comprising: culturing a microorganism of the genus *Corynebacterium* expressing a NADP-dependent glyceraldehyde-3-phosphate dehydrogenase comprising the amino acid sequence of SEQ ID NO: 1, in a medium to produce said L-amino acid; and recovering an L-amino acid from the cultured microorganism or cultured medium.

2. The method of claim 1, wherein the NADP-dependent glyceraldehyde-3-phosphate dehydrogenase is encoded by the nucleotide sequence of SEQ ID NO: 2.

3. The method of claim 1, wherein the microorganism of the genus *Corynebacterium* is *Corynebacterium glutamicum*.

4. A microorganism of the genus *Corynebacterium* modified to express a NADP-dependent glyceraldehyde-3-phosphate dehydrogenase comprising the amino acid sequence of SEQ ID NO: 1.

5. The microorganism of claim 4, wherein the microorganism of the genus *Corynebacterium* is *Corynebacterium glutamicum*.

6. The microorganism of claim 4, wherein the microorganism has an increased L-amino acid producing ability compared to a non-modified microorganism.

7. A microorganism of the genus *Corynebacterium* comprising a vector, wherein said vector comprises a nucleotide molecule encoding a NADP-dependent glyceraldehyde-3-phosphate dehydrogenase comprising the amino acid sequence of SEQ ID NO: 1.

8. The microorganism of claim 7, wherein the nucleotide molecule comprises the nucleotide sequence of SEQ ID NO: 2.

9. A method of increasing an L-amino acid producing ability of a microorganism of the genus *Corynebacterium* as compared to a non-modified microorganism, the method comprising; modifying the microorganism to express a NADP-dependent glyceraldehyde-3-phosphate dehydrogenase including comprising the amino acid sequence of SEQ ID NO: 1; and culturing the modified microorganism, thereby increasing the L-amino acid producing ability of the microorganism.

10. A method of increasing an L-amino acid producing ability of a microorganism of the genus *Corynebacterium* as compared to a non-modified microorganism, the method comprising; modifying the microorganism to comprise a vector comprising the nucleotide molecule encoding the amino acid sequence of SEQ ID NO: 1; and culturing the modified microorganism, thereby increasing the L amino acid producing ability of the microorganism.

11. The method of claim 1, wherein the microorganism of the genus *Corynebacterium* is *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, or *Corynebacterium flavescens*.

12. The microorganism of claim 4, wherein the microorganism of the genus *Corynebacterium* is *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium pollutisoli*, *Corynebacterium imitans*, *Corynebacterium testudinoris*, or *Corynebacterium flavescens*.

13. The method of claim 1, wherein the L-amino acid comprises at least one L-amino acid selected from the group consisting of L-arginine, L-histidine, L-lysine, L-aspartic acid, L-glutamic acid, L-serine, L-threonine, L-asparagine, L-glutamine, L-tyrosine, L-alanine, L-isoleucine, L-leucine, L-valine, L-phenylalanine, L-methionine, L-tryptophan, glycine, L-proline, and L-cysteine.

14. The method of claim 1, wherein the L-amino acid is L-lysine, L-threonine, L-isoleucine, L-leucine, L-valine, L-arginine, or L-glutamic acid.

15. The method of claim 9, wherein the L-amino acid is L-lysine, L-threonine, L-isoleucine, L-leucine, L-valine, L-arginine, or L-glutamic acid.

16. The method of claim 10, wherein the L-amino acid is L-lysine, L-threonine, L-isoleucine, L-leucine, L-valine, L-arginine, or L-glutamic acid.

17. The method of claim 9, wherein the microorganism of the genus *Corynebacterium* is *Corynebacterium glutamicum*, *Corynebacterium ammoniagenes*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium*

*pollutisoli, Corynebacterium imitans, Corynebacterium testudinoris,* or *Corynebacterium flavescens.*

18. The method of claim 10, wherein the microorganism of the genus *Corynebacterium* is *Corynebacterium glutamicum, Corynebacterium ammoniagenes, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium pollutisoli, Corynebacterium imitans, Corynebacterium testudinoris,* or *Corynebacterium flavescens.*

19. The method of claim 9, wherein the L-amino acid comprises at least one L-amino acid selected from the group consisting of L-lysine, L-threonine, L-isoleucine, L-leucine, L-valine, L-arginine, and L-glutamic acid.

20. The method of claim 10, wherein the L-amino acid comprises at least one L-amino acid selected from the group consisting of L-lysine, L-threonine, L-isoleucine, L-leucine, L-valine, L-arginine, and L-glutamic acid.

* * * * *

```
                        SEQUENCE LISTING

<160> NUMBER OF SEQ ID NOS: 39

<210> SEQ ID NO 1
<211> LENGTH: 476
<212> TYPE: PRT
<213> ORGANISM: Unknown
<220> FEATURE:
<223> OTHER INFORMATION: Lactobacillus delbrueckii subsp. Bulgaricus
      gapN amino acid

<400> SEQUENCE: 1

Met Thr Glu His Tyr Leu Asn Tyr Val Asn Gly Glu Trp Arg Asp Ser
1               5                   10                  15

Ala Asp Ala Ile Glu Ile Phe Glu Pro Ala Thr Gly Lys Ser Leu Gly
                20                  25                  30

Thr Val Pro Ala Met Ser His Glu Asp Val Asp Tyr Val Met Asn Ser
            35                  40                  45

Ala Lys Lys Ala Leu Pro Ala Trp Arg Ala Leu Ser Tyr Val Glu Arg
    50                  55                  60

Ala Ala Tyr Leu Gln Lys Ala Asp Ile Leu Tyr Arg Asp Ala Glu
65                  70                  75                  80

Lys Ile Gly Ser Thr Leu Ser Lys Glu Ile Ala Lys Gly Leu Lys Ser
                85                  90                  95

Ser Ile Gly Glu Val Thr Arg Thr Ala Glu Ile Val Glu Tyr Thr Ala
            100                 105                 110

Lys Val Gly Val Thr Leu Asp Gly Glu Val Met Glu Gly Gly Asn Phe
        115                 120                 125

Glu Ala Ala Ser Lys Asn Lys Leu Ala Val Val Arg Arg Glu Pro Val
    130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Met Gly Gly Asn Val Val Ala Phe
                165                 170                 175

Lys Pro Pro Thr Gln Gly Ser Ile Ser Gly Leu Leu Ala Lys Ala
            180                 185                 190

Phe Ala Glu Ala Gly Leu Pro Ala Gly Val Phe Asn Thr Ile Thr Gly
        195                 200                 205

Arg Gly Arg Val Ile Gly Asp Tyr Ile Val Glu His Pro Ala Val Asn
    210                 215                 220

Phe Ile Asn Phe Thr Gly Ser Ser Ala Val Gly Lys Asn Ile Gly Lys
225                 230                 235                 240

Leu Ala Gly Met Arg Pro Ile Met Leu Glu Leu Gly Gly Lys Asp Ala
                245                 250                 255

Ala Ile Val Leu Glu Asp Ala Asp Leu Asp Leu Thr Ala Lys Asn Ile
            260                 265                 270

Val Ala Gly Ala Phe Gly Tyr Ser Gly Gln Arg Cys Thr Ala Val Lys
        275                 280                 285

Arg Val Leu Val Met Asp Ser Val Ala Asp Glu Leu Val Glu Lys Val
    290                 295                 300
```

Thr Ala Leu Ala Lys Asp Leu Thr Val Gly Ile Pro Glu Glu Asp Ala
305                 310                 315                 320

Asp Ile Thr Pro Leu Ile Asp Thr Lys Ser Ala Asp Tyr Val Gln Gly
            325                 330                 335

Leu Ile Glu Glu Ala Ala Glu Lys Gly Ala Lys Pro Leu Phe Asp Phe
            340                 345                 350

Lys Arg Glu Gly Asn Leu Ile Tyr Pro Met Val Met Asp Gln Val Thr
            355                 360                 365

Thr Asp Met Arg Leu Ala Trp Glu Glu Pro Phe Gly Pro Val Leu Pro
370                 375                 380

Phe Ile Arg Val Lys Ser Ala Asp Glu Ala Val Met Ile Ala Asn Glu
385                 390                 395                 400

Ser Glu Tyr Gly Leu Gln Ser Ser Val Phe Ser Arg Asn Phe Glu Lys
            405                 410                 415

Ala Phe Ala Ile Ala Gly Lys Leu Glu Val Gly Thr Val His Ile Asn
            420                 425                 430

Asn Lys Thr Gln Arg Gly Pro Asp Asn Phe Pro Phe Leu Gly Val Lys
            435                 440                 445

Ser Ser Gly Ala Gly Val Gln Gly Val Lys Tyr Ser Ile Gln Ala Met
    450                 455                 460

Thr Arg Val Lys Ser Val Val Phe Asn Ile Glu Asp
465                 470                 475

<210> SEQ ID NO 2
<211> LENGTH: 1431
<212> TYPE: DNA
<213> ORGANISM: Unknown
<220> FEATURE:
<223> OTHER INFORMATION: Lactobacillus delbrueckii subsp. Bulgaricus
      gapN nucleotide

<400> SEQUENCE: 2
atgacagaac actatttaaa ctatgtcaat ggcgaatggc gggactccgc tgacgcgatt     60 gaaatttttcg aaccagcaac tggcaagtcc ctgggtactg tacctgccat gtcccacgaa    120
gacgtggact acgtaatgaa cagcgccaaa aaggcccttc cagcctggcg ggccctctca    180
tacgttgaac gggccgcata cttgcaaaag gcagcggaca tccttaccg agatgctgaa     240 aagatcggtt ctaccttgtc caaggaaatc gccaagggcc tcaagtcctc tatcggcgaa    300
gtaacccgga cggcggaaat cgttgaatac acggccaagg tcggcgtaac tttggacggg    360
gaagtcatgg agggcggcaa ctttgaagcg caagcaaga acaagttggc tgttgtccgc    420
cgggaaccag tcggcctggt ttttggcaatt tcacccttca actacccggt taacctggcc    480
ggctcaaaga tcgcgcctgc tttgatgggc gggaacgtgg tggccttcaa gccgccgaca    540
caagggtcaa tctccggtct gcttttggcc aaggccttcg ccgaagctgg cctgccagcc    600
ggcgtcttca acaccattac cggccggggt cgggttatcg cgactacat cgttgaacac     660 ccggcagtca acttcatcaa cttcaccggt tccagtgctg tcggcaagaa catcggcaaa    720
ctggccggga tgcggccgat tatgctggaa cttggcggca aggacgcggc catcgtcttg    780
gaagacgctg acttggacct gacggccaag aacatcgttg ccggcgcctt tggctactcc    840
ggccagcgtt gtaccgccgt taagcgggtt ctggtcatgg acagcgtggc tgacgaattg    900
gttgaaaagg tgactgcttt ggccaaggat ttgacggtcg ggataccaga agaggatgcc    960
gacatcactc ctttgatcga cactaagtct gccgactacg tacaaggctt aattgaagaa   1020

-continued

```
gccgcagaaa agggcgctaa gcctttgttt gacttcaagc gcgaaggcaa cctgatctac    1080
ccaatggtca tggaccaagt gacgactgac atgcgcctgg cctgggaaga accatttgga    1140
ccagtattgc cattcatccg cgtcaagtca gctgacgaag ctgtcatgat tgccaatgaa    1200
tcagaatacg gccttcaaag ctccgtcttc tcacggaact ttgaaaaagc ctttgccatt    1260
gcaggaaaat tggaagtggg cacggtccac atcaacaaca agacccaaag aggtccggac    1320
aacttcccat tcctgggcgt aaagagctca ggggcaggcg tacagggggt caagtactcc    1380
attcaagcca tgacccgggt caagtccgtt gtcttcaaca tcgaagacta a              1431
```

<210> SEQ ID NO 3
<211> LENGTH: 40
<212> TYPE: DNA
<213> ORGANISM: Artificial Sequence
<220> FEATURE:
<223> OTHER INFORMATION: gapN F

<400> SEQUENCE: 3

```
cccaacgaaa ggaaacactc atgacagaac actatttaaa                          40
```

<210> SEQ ID NO 4
<211> LENGTH: 45
<212> TYPE: DNA
<213> ORGANISM: Artificial Sequence
<220> FEATURE:
<223> OTHER INFORMATION: gapN R

<400> SEQUENCE: 4

```
gcttgtgaat aagcctgccc ttagtcttcg atgttgaaga caacg                    45
```

<210> SEQ ID NO 5
<211> LENGTH: 40
<212> TYPE: DNA
<213> ORGANISM: Artificial Sequence
<220> FEATURE:
<223> OTHER INFORMATION: Pcj7 F

<400> SEQUENCE: 5

```
gattccaggt tccttaaccc agaaacatcc cagcgctact                          40
```

<210> SEQ ID NO 6
<211> LENGTH: 40
<212> TYPE: DNA
<213> ORGANISM: Artificial Sequence
<220> FEATURE:
<223> OTHER INFORMATION: Pcj7 R

<400> SEQUENCE: 6

```
tttaaatagt gttctgtcat gagtgtttcc tttcgttggg                          40
```

<210> SEQ ID NO 7
<211> LENGTH: 40
<212> TYPE: DNA
<213> ORGANISM: Artificial Sequence
<220> FEATURE:
<223> OTHER INFORMATION: Ldb1179 R

<400> SEQUENCE: 7

```
tttcgtgcga gtctagaagt ttagtcttcg atgttgaaga                          40
```

<210> SEQ ID NO 8
<211> LENGTH: 40
<212> TYPE: DNA
<213> ORGANISM: Artificial Sequence

```
<220> FEATURE:
<223> OTHER INFORMATION: Pcj7_2 F

<400> SEQUENCE: 8
acgaggtcag catctcgagt agaaacatcc cagcgctact                              40

<210> SEQ ID NO 9
<211> LENGTH: 36
<212> TYPE: DNA
<213> ORGANISM: Artificial Sequence
<220> FEATURE:
<223> OTHER INFORMATION: Pcj7_3 F

<400> SEQUENCE: 9
cgcggaactg tactagtaga aacatcccag cgctac                                  36

<210> SEQ ID NO 10
<211> LENGTH: 34
<212> TYPE: DNA
<213> ORGANISM: Artificial Sequence
<220> FEATURE:
<223> OTHER INFORMATION: Ldb1179_2 R

<400> SEQUENCE: 10
ggaaggatat ctctagaaga taaaacgaaa ggcc                                    34

<210> SEQ ID NO 11
<211> LENGTH: 36
<212> TYPE: DNA
<213> ORGANISM: Artificial Sequence
<220> FEATURE:
<223> OTHER INFORMATION: Pcj7_4 F

<400> SEQUENCE: 11
cccttccggt ttagtactag aaacatccca gcgcta                                  36

<210> SEQ ID NO 12
<211> LENGTH: 37
<212> TYPE: DNA
<213> ORGANISM: Artificial Sequence
<220> FEATURE:
<223> OTHER INFORMATION: Ldb1179_3 R

<400> SEQUENCE: 12
ctcttcctgt ttagtacttt agtcttcgat gttgaag                                 37

<210> SEQ ID NO 13
<211> LENGTH: 475
<212> TYPE: PRT
<213> ORGANISM: Unknown
<220> FEATURE:
<223> OTHER INFORMATION: Streptococcus mutans gapN amino acid

<400> SEQUENCE: 13
```

Met Thr Lys Gln Tyr Lys Asn Tyr Val Asn Gly Glu Trp Lys Leu Ser
 1               5                  10                  15

Glu Asn Glu Ile Lys Ile Tyr Glu Pro Ala Ser Gly Ala Glu Leu Gly
             20                  25                  30

Ser Val Pro Ala Met Ser Thr Glu Glu Val Asp Tyr Val Tyr Ala Ser
         35                  40                  45

Ala Lys Lys Ala Gln Pro Ala Trp Arg Ser Leu Ser Tyr Ile Glu Arg
     50                  55                  60

Ala Ala Tyr Leu His Lys Val Ala Asp Ile Leu Met Arg Asp Lys Glu
 65                  70                  75                  80

```
Lys Ile Gly Ala Val Leu Ser Lys Glu Val Ala Lys Gly Tyr Lys Ser
                85                  90                  95

Ala Val Ser Glu Val Val Arg Thr Ala Glu Ile Ile Asn Tyr Ala Ala
               100                 105                 110

Glu Glu Gly Leu Arg Met Glu Gly Val Leu Glu Gly Gly Ser Phe
               115                 120                 125

Glu Ala Ala Ser Lys Lys Ile Ala Val Val Arg Arg Glu Pro Val
130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Ile Ala Gly Asn Val Ile Ala Phe
               165                 170                 175

Lys Pro Pro Thr Gln Gly Ser Ile Ser Gly Leu Leu Leu Ala Glu Ala
               180                 185                 190

Phe Ala Glu Ala Gly Leu Pro Ala Gly Val Phe Asn Thr Ile Thr Gly
               195                 200                 205

Arg Gly Ser Glu Ile Gly Asp Tyr Ile Val Glu His Gln Ala Val Asn
210                 215                 220

Phe Ile Asn Phe Thr Gly Ser Thr Gly Ile Gly Glu Arg Ile Gly Lys
225                 230                 235                 240

Met Ala Gly Met Arg Pro Ile Met Leu Glu Leu Gly Gly Lys Asp Ser
                    245                 250                 255

Ala Ile Val Leu Glu Asp Ala Asp Leu Glu Leu Thr Ala Lys Asn Ile
               260                 265                 270

Ile Ala Gly Ala Phe Gly Tyr Ser Gly Gln Arg Cys Thr Ala Val Lys
               275                 280                 285

Arg Val Leu Val Met Glu Ser Val Ala Asp Glu Leu Val Glu Lys Ile
               290                 295                 300

Arg Glu Lys Val Leu Ala Leu Thr Ile Gly Asn Pro Glu Asp Asp Ala
305                 310                 315                 320

Asp Ile Thr Pro Leu Ile Asp Thr Lys Ser Ala Asp Tyr Val Glu Gly
               325                 330                 335

Leu Ile Asn Asp Ala Asn Asp Lys Gly Ala Ala Leu Thr Glu Ile
               340                 345                 350

Lys Arg Glu Gly Asn Leu Ile Cys Pro Ile Leu Phe Asp Lys Val Thr
               355                 360                 365

Thr Asp Met Arg Leu Ala Trp Glu Glu Pro Phe Gly Pro Val Leu Pro
               370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                    405                 410                 415

Ala Phe Gly Ile Ala Glu Gln Leu Glu Val Gly Thr Val His Ile Asn
                    420                 425                 430

Asn Lys Thr Gln Arg Gly Thr Asp Asn Phe Pro Phe Leu Gly Ala Lys
               435                 440                 445

Lys Ser Gly Ala Gly Ile Gln Gly Val Lys Tyr Ser Ile Glu Ala Met
450                 455                 460

Thr Thr Val Lys Ser Val Val Phe Asp Ile Lys
465                 470                 475

<210> SEQ ID NO 14
<211> LENGTH: 1428
```

```
<212> TYPE: DNA
<213> ORGANISM: Unknown
<220> FEATURE:
<223> OTHER INFORMATION: Streptococcus mutans gapN nucleotide

<400> SEQUENCE: 14
atgacaaaac aatataaaaa ttatgtcaat ggcgagtgga agctttcaga aaatgaaatt      60
aaaatctacg aaccggccag tggagctgaa ttgggttcag ttccagcaat gagtactgaa     120
gaagtagatt atgtttatgc ttcagccaag aaagctcaac cagcttggcg atcactttca     180
tacatagaac gtgctgccta ccttcacaag gtagcagata ttttgatgcg tgataaagaa     240
aaaataggtg ctgttctttc caaagaggtt gctaaaggtt ataaatcagc agtcagcgaa     300
gttgttcgta ctgcagaaat cattaattat gcagctgaag aaggccttcg tatggaaggt     360
gaagtccttg aaggcggcag ttttgaagca gccagcaaga aaaaaattgc cgttgttcgt     420
cgtgaaccag taggtcttgt attagctatt tcaccattta actaccctgt aacttggca      480
ggttcgaaaa ttgcaccggc tcttattgcg ggaaatgtta ttgcttttaa accaccgacg     540
caaggatcaa tctcagggct cttacttgct gaagcatttg ctgaagctgg acttcctgca     600
ggtgtcttta ataccattac aggtcgtggt tctgaaattg gagactatat tgtagaacat     660
caagccgtta actttatcaa ttttactggt tcaacaggaa ttggggaacg tattggcaaa     720
atggctggta tgcgtccgat tatgcttgaa ctcggtggaa agattcagc catcgttctt     780
gaagatgcag accttgaatt gactgctaaa atattattg caggtgcttt tggttattca     840
ggtcaacgct gtacagcagt taaacgtgtt cttgtgatgg aaagtgttgc tgatgaactg     900
gtcgaaaaaa tccgtgaaaa agttcttgca ttaacaattg gtaatccaga agacgatgca     960
gatattacac cgttgattga tacaaaatca gctgattatg tagaaggtct tattaatgat    1020
gccaatgata aaggagccgc tgcccttact gaaatcaaac gtgaaggtaa tcttatctgt    1080
ccaatcctct ttgataaggt aacgacagat atgcgtcttg cttgggaaga accatttggt    1140
cctgttcttc cgatcattcg tgtgacatct gtagaagaag ccattgaaat ttctaacaaa    1200
tcggaatatg gacttcaggc ttctatcttt acaaatgatt tcccacgcgc ttttggtatt    1260
gctgagcagc ttgaagttgg tacagttcat atcaataata agacacagcg cggcacggac    1320
aacttcccat tcttaggggc taaaaaatca ggtgcaggta ttcaagggggt aaaatattct    1380
attgaagcta tgacaactgt taaatccgtc gtatttgata tcaaataa                 1428

<210> SEQ ID NO 15
<211> LENGTH: 40
<212> TYPE: DNA
<213> ORGANISM: Artificial Sequence
<220> FEATURE:
<223> OTHER INFORMATION: Pcj7-gapN1 F

<400> SEQUENCE: 15
tagatgtcgg gccccatatg agaaacatcc cagcgctact                            40

<210> SEQ ID NO 16
<211> LENGTH: 45
<212> TYPE: DNA
<213> ORGANISM: Artificial Sequence
<220> FEATURE:
<223> OTHER INFORMATION: Pcj7-gapN1 R

<400> SEQUENCE: 16
gccaaaacag cctcgagtta tttgatatca aatacgacgg attta                      45
```

```
<210> SEQ ID NO 17
<211> LENGTH: 29
<212> TYPE: DNA
<213> ORGANISM: Artificial Sequence
<220> FEATURE:
<223> OTHER INFORMATION: lysC-1 F

<400> SEQUENCE: 17
tcctctagag ctgcgcagtg ttgaatacg                                29

<210> SEQ ID NO 18
<211> LENGTH: 30
<212> TYPE: DNA
<213> ORGANISM: Artificial Sequence
<220> FEATURE:
<223> OTHER INFORMATION: lysC-1 R

<400> SEQUENCE: 18
tggaaatctt ttcgatgttc acgttgacat                               30

<210> SEQ ID NO 19
<211> LENGTH: 30
<212> TYPE: DNA
<213> ORGANISM: Artificial Sequence
<220> FEATURE:
<223> OTHER INFORMATION: lysC-2 F

<400> SEQUENCE: 19
acatcgaaaa gatttccacc tctgagattc                               30

<210> SEQ ID NO 20
<211> LENGTH: 29
<212> TYPE: DNA
<213> ORGANISM: Artificial Sequence
<220> FEATURE:
<223> OTHER INFORMATION: lysC-2 R

<400> SEQUENCE: 20
gactctagag ttcacctcag agacgatta                                29

<210> SEQ ID NO 21
<211> LENGTH: 29
<212> TYPE: DNA
<213> ORGANISM: Artificial Sequence
<220> FEATURE:
<223> OTHER INFORMATION: Hom-1 F

<400> SEQUENCE: 21
tcctctagac tggtcgcctg atgttctac                                29

<210> SEQ ID NO 22
<211> LENGTH: 20
<212> TYPE: DNA
<213> ORGANISM: Artificial Sequence
<220> FEATURE:
<223> OTHER INFORMATION: Hom-1 R

<400> SEQUENCE: 22
ctcttcctgt tggattgtac                                          20

<210> SEQ ID NO 23
<211> LENGTH: 20
<212> TYPE: DNA
<213> ORGANISM: Artificial Sequence
<220> FEATURE:
<223> OTHER INFORMATION: Hom-2 F
```

```
<400> SEQUENCE: 23 gtacaatccca acaggaagag                                                  20

<210> SEQ ID NO 24
<211> LENGTH: 29
<212> TYPE: DNA
<213> ORGANISM: Artificial Sequence
<220> FEATURE:
<223> OTHER INFORMATION: Hom-2 R

<400> SEQUENCE: 24
gactctagat tagtcccttt cgaggcgga                                         29

<210> SEQ ID NO 25
<211> LENGTH: 28
<212> TYPE: DNA
<213> ORGANISM: Artificial Sequence
<220> FEATURE:
<223> OTHER INFORMATION: ilvA-1 F

<400> SEQUENCE: 25
acggatccca gactccaaag caaaagcg                                          28

<210> SEQ ID NO 26
<211> LENGTH: 30
<212> TYPE: DNA
<213> ORGANISM: Artificial Sequence
<220> FEATURE:
<223> OTHER INFORMATION: ilvA-1 R

<400> SEQUENCE: 26
acaccacggc agaaccaggt gcaaaggaca                                        30

<210> SEQ ID NO 27
<211> LENGTH: 30
<212> TYPE: DNA
<213> ORGANISM: Artificial Sequence
<220> FEATURE:
<223> OTHER INFORMATION: ilvA-2 F

<400> SEQUENCE: 27
ctggttctgc cgtggtgtgc atcatctctg                                        30

<210> SEQ ID NO 28
<211> LENGTH: 28
<212> TYPE: DNA
<213> ORGANISM: Artificial Sequence
<220> FEATURE:
<223> OTHER INFORMATION: ilvA-2 R

<400> SEQUENCE: 28
acggatccaa ccaaacttgc tcacactc                                          28

<210> SEQ ID NO 29
<211> LENGTH: 32
<212> TYPE: DNA
<213> ORGANISM: Artificial Sequence
<220> FEATURE:
<223> OTHER INFORMATION: ilvN-1 F

<400> SEQUENCE: 29
aatttctaga ggcagaccct attctatgaa gg                                     32

<210> SEQ ID NO 30
```

```
<211> LENGTH: 30
<212> TYPE: DNA
<213> ORGANISM: Artificial Sequence
<220> FEATURE:
<223> OTHER INFORMATION: ilvN-1 R

<400> SEQUENCE: 30
agtgtttcgg tctttacaga cacgagggac                                      30

<210> SEQ ID NO 31
<211> LENGTH: 30
<212> TYPE: DNA
<213> ORGANISM: Artificial Sequence
<220> FEATURE:
<223> OTHER INFORMATION: ilvN-2 F

<400> SEQUENCE: 31
gtccctcgtg tctgtaaaga ccgaaacact                                      30

<210> SEQ ID NO 32
<211> LENGTH: 32
<212> TYPE: DNA
<213> ORGANISM: Artificial Sequence
<220> FEATURE:
<223> OTHER INFORMATION: ilvN-2 R

<400> SEQUENCE: 32
aatttctaga cgtgggagtg tcactcgctt gg                                   32

<210> SEQ ID NO 33
<211> LENGTH: 28
<212> TYPE: DNA
<213> ORGANISM: Artificial Sequence
<220> FEATURE:
<223> OTHER INFORMATION: MetX F

<400> SEQUENCE: 33
ggatcccctc gttgttcacc cagcaacc                                        28

<210> SEQ ID NO 34
<211> LENGTH: 30
<212> TYPE: DNA
<213> ORGANISM: Artificial Sequence
<220> FEATURE:
<223> OTHER INFORMATION: MetX R

<400> SEQUENCE: 34
ggatcccaaa gtcacaacta cttatgttag                                      30

<210> SEQ ID NO 35
<211> LENGTH: 482
<212> TYPE: PRT
<213> ORGANISM: Unknown
<220> FEATURE:
<223> OTHER INFORMATION: Clostridium acetobutylicum gapN amino acid

<400> SEQUENCE: 35

Met Phe Glu Asn Ile Ser Ser Asn Gly Val Tyr Lys Asn Leu Phe Asp
1               5                   10                  15

Gly Lys Trp Val Glu Ser Lys Thr Asn Lys Thr Ile Glu Thr His Ser
            20                  25                  30

Pro Tyr Asp Gly Ser Leu Ile Gly Lys Val Gln Ala Leu Ser Lys Glu
        35                  40                  45

Glu Val Asp Glu Ile Phe Lys Ser Ser Arg Thr Ala Gln Lys Lys Trp
    50                  55                  60
```

```
Gly Glu Thr Pro Ile Asn Glu Arg Ala Arg Ile Met Arg Lys Ala Ala
 65                  70                  75                  80

Asp Ile Leu Asp Asp Asn Ala Glu Tyr Ile Ala Lys Ile Leu Ser Asn
                 85                  90                  95

Glu Ile Ala Lys Asp Leu Lys Ser Ser Leu Ser Glu Val Lys Arg Thr
            100                 105                 110

Ala Asp Phe Ile Arg Phe Thr Ala Asn Glu Gly Thr His Met Glu Gly
        115                 120                 125

Glu Ala Ile Asn Ser Asp Asn Phe Pro Gly Ser Lys Lys Asp Lys Leu
    130                 135                 140

Ser Leu Val Glu Arg Val Pro Leu Gly Ile Val Leu Ala Ile Ser Pro
145                 150                 155                 160

Phe Asn Tyr Pro Val Asn Leu Ser Gly Ser Lys Val Ala Pro Ala Leu
                165                 170                 175

Ile Ala Gly Asn Ser Val Val Leu Lys Pro Ser Thr Thr Gly Ala Ile
            180                 185                 190

Ser Ala Leu His Leu Ala Glu Ile Phe Asn Ala Ala Gly Leu Pro Ala
        195                 200                 205

Gly Val Leu Asn Thr Val Thr Gly Lys Gly Ser Glu Ile Gly Asp Tyr
    210                 215                 220

Leu Ile Thr His Glu Glu Val Asn Phe Ile Asn Phe Thr Gly Ser Ser
225                 230                 235                 240

Ala Val Gly Lys His Ile Ser Lys Ile Ala Gly Met Ile Pro Met Val
                245                 250                 255

Leu Glu Leu Gly Gly Lys Asp Ala Ala Ile Val Leu Glu Asp Ala Asn
            260                 265                 270

Leu Glu Thr Thr Ala Lys Ser Ile Val Ser Gly Ala Tyr Gly Tyr Ser
        275                 280                 285

Gly Gln Arg Cys Thr Ala Val Lys Arg Val Leu Val Met Asp Lys Val
    290                 295                 300

Ala Asp Glu Leu Val Glu Leu Val Thr Lys Val Lys Glu Leu Lys
305                 310                 315                 320

Val Gly Asn Pro Phe Asp Asp Val Thr Ile Thr Pro Leu Ile Asp Asn
                325                 330                 335

Lys Ala Ala Asp Tyr Val Gln Thr Leu Ile Asp Asp Ala Ile Glu Lys
            340                 345                 350

Gly Ala Thr Leu Ile Val Gly Asn Lys Arg Lys Glu Asn Leu Met Tyr
        355                 360                 365

Pro Thr Leu Phe Asp Asn Val Thr Ala Asp Met Arg Ile Ala Trp Glu
    370                 375                 380

Glu Pro Phe Gly Pro Val Leu Pro Ile Ile Arg Val Lys Ser Met Asp
385                 390                 395                 400

Glu Ala Ile Glu Leu Ala Asn Arg Ser Glu Tyr Gly Leu Gln Ser Ala
                405                 410                 415

Val Phe Thr Glu Asn Met His Asp Ala Phe Tyr Ile Ala Asn Lys Leu
            420                 425                 430

Asp Val Gly Thr Val Gln Val Asn Asn Lys Pro Glu Arg Gly Pro Asp
        435                 440                 445

His Phe Pro Phe Leu Gly Thr Lys Ser Ser Gly Met Gly Thr Gln Gly
    450                 455                 460
```

Ile Arg Tyr Ser Ile Glu Ala Met Thr Arg His Lys Ser Ile Val Leu
465                 470                 475                 480

Asn Leu

<210> SEQ ID NO 36
<211> LENGTH: 1449
<212> TYPE: DNA
<213> ORGANISM: Unknown
<220> FEATURE:
<223> OTHER INFORMATION: Clostridium acetobutylicum gapN nucleotide

<400> SEQUENCE: 36

| | | | | | |
|---|---|---|---|---|---|
| atgtttgaaa | atatatcatc | aaatggagtt | tataaaaatc | tatttgatgg | aaaatgggtt | 60 |
| gaaagtaaga | caaataaaac | catagaaacg | cattctcctt | atgatggaag | tttaattgga | 120 |
| aaagttcagg | ccttatcaaa | agaggaagtt | gatgagattt | taaaagttc | aagaacagct | 180 |
| cagaaaaaat | ggggtgaaac | tccaataaat | gagcgtgcta | gaatcatgcg | taaagcagct | 240 |
| gatatactag | atgataacgc | agaatatata | gcaaaaattc | tttcaaatga | gatagcaaaa | 300 |
| gatttaaaat | cttctctttc | agaagtaaaa | agaacagctg | attttataag | atttacagct | 360 |
| aatgaaggta | ctcatatgga | aggagaagct | attaactcag | ataattttcc | tggttctaaa | 420 |
| aaagataaac | tttctctagt | tgaaagagtt | cctttaggaa | tagttttagc | tatatctcct | 480 |
| tttaattatc | ctgtaaatct | ttctgggtct | aaggttgctc | cagcacttat | agctggaaat | 540 |
| agtgttgttt | taaaaccttc | tacaactggt | gctataagcg | cacttcatct | tgcagaaatt | 600 |
| tttaatgcag | ctggtcttcc | agcaggtgtt | taaacactg | taacaggaaa | agggtctgaa | 660 |
| ataggcgatt | atttaattac | ccatgaagaa | gtaaacttta | ttaactttac | gggaagctct | 720 |
| gctgtaggta | agcatatttc | aaaaatagct | ggaatgatac | ctatggttct | tgagcttggt | 780 |
| ggtaaagatg | ctgctatagt | tctcgaagat | gccaatcttg | aaacaacagc | taaaagcata | 840 |
| gtatctggag | catatggata | ctccggccaa | aggtgtactg | ctgtaaaaag | agttcttgta | 900 |
| atggataaag | tagctgatga | attagttgaa | cttgttacaa | aaaaagttaa | agaattaaag | 960 |
| gtaggtaatc | cttttgatga | tgttacaata | accccactta | tagacaacaa | ggcagcagat | 1020 |
| tatgttcaaa | ctctcattga | cgacgctatc | gaaaagggtg | caactcttat | cgttggaaat | 1080 |
| aagcgtaaag | aaaatttaat | gtatcctact | ttatttgata | atgtaactgc | tgatatgcgt | 1140 |
| attgcttggg | aagaaccatt | tggaccagtt | ttacctatta | ttcgtgtaaa | aagcatggat | 1200 |
| gaagcaatag | aattagcaaa | tagatctgaa | atggtcttc | aatctgcagt | atttactgaa | 1260 |
| aatatgcatg | atgccttta | tattgccaat | aaattagatg | ttggaactgt | tcaagtaaat | 1320 |
| aataagcctg | aaagaggccc | agatcacttc | ccattccttg | aacaaagtc | atcaggtatg | 1380 |
| ggcactcaag | gaattcgata | cagtatagag | gcaatgacaa | ggcataaatc | aatagtttta | 1440 |
| aacctataa | | | | | | 1449 |

<210> SEQ ID NO 37
<211> LENGTH: 44
<212> TYPE: DNA
<213> ORGANISM: Artificial Sequence
<220> FEATURE:
<223> OTHER INFORMATION: gapN F

<400> SEQUENCE: 37
acccaacgaa aggaaacact catgtttgaa aatatatcat caaa        44

```
<210> SEQ ID NO 38
<211> LENGTH: 40
<212> TYPE: DNA
<213> ORGANISM: Artificial Sequence
<220> FEATURE:
<223> OTHER INFORMATION: gapN R

<400> SEQUENCE: 38
gccaaaacag cctcgagtta taggtttaaa actattgatt                              40

<210> SEQ ID NO 39
<211> LENGTH: 44
<212> TYPE: DNA
<213> ORGANISM: Artificial Sequence
<220> FEATURE:
<223> OTHER INFORMATION: gapN R

<400> SEQUENCE: 39
tttgatgata tattttcaaa catgagtgtt tcctttcgtt gggt                         44
```